United States Patent
Teramura et al.

(10) Patent No.: US 7,864,331 B2
(45) Date of Patent: *Jan. 4, 2011

(54) OPTICAL COHERENCE TOMOGRAPHIC IMAGING APPARATUS

(75) Inventors: Yuichi Teramura, Kanagawa-ken (JP); Sadato Akahori, Kanagawa-ken (JP); Yoshikatsu Morishima, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 91 days.

This patent is subject to a terminal disclaimer.

(21) Appl. No.: 11/941,481

(22) Filed: Nov. 16, 2007

(65) Prior Publication Data

US 2008/0117424 A1    May 22, 2008

(30) Foreign Application Priority Data

Nov. 17, 2006   (JP)   ............................ 2006-311285
Nov. 15, 2007   (JP)   ............................ 2007-296456

(51) Int. Cl.
    G01B 9/02    (2006.01)
(52) U.S. Cl. .................................... 356/479
(58) Field of Classification Search ................ 356/477, 356/479, 497
    See application file for complete search history.

(56) References Cited

U.S. PATENT DOCUMENTS

| | | | |
|---|---|---|---|
| 5,321,501 A * | 6/1994 | Swanson et al. ............ | 356/479 |
| 5,892,583 A * | 4/1999 | Li ............................... | 356/479 |
| 6,184,542 B1 * | 2/2001 | Alphonse ...................... | 257/94 |
| 6,538,817 B1 | 3/2003 | Farmer et al. | |
| 7,538,884 B2 * | 5/2009 | Teramura et al. ............ | 356/489 |
| 2005/0018201 A1 | 1/2005 | de Boer | |
| 2006/0079762 A1 * | 4/2006 | Norris et al. ................ | 600/427 |
| 2006/0146338 A1 | 7/2006 | Fujita | |
| 2006/0146339 A1 | 7/2006 | Fujita | |

(Continued)

FOREIGN PATENT DOCUMENTS

EP   1 666 838 A1   6/2006

(Continued)

OTHER PUBLICATIONS

Kinoshita et al., "Optical frequency-domain imaging microprofilometry with a frequency-tunable liquid-crystal Fabry-Perot etalon device," Applied Optics, vol. 38, No. 34, Dec. 1, 1999, pp. 7063-7068, XP000893806.

(Continued)

*Primary Examiner*—Samuel A Turner
(74) *Attorney, Agent, or Firm*—Sughrue Mion, PLLC

(57) ABSTRACT

A first light beam and a second light beam having discrete wavelength bands are emitted form a light source unit, and enter a light divider. The light divider separates each light beam into a measuring light beam and a reference light beam. The measuring light beams are irradiated on a measurement target, and reflected light beams, which are reflected at various depth positions of the measurement target, are caused to enter a combiner. The reference light beams propagate through optical fibers to enter the combiner. Interference light beams formed by the reflected light beams and the reference light beams for each of the first and second light beams are photoelectrically converted into interference signals. A tomographic image is obtained employing the interference signals for each of the first and second light beams.

8 Claims, 9 Drawing Sheets

U.S. PATENT DOCUMENTS

2007/0024856 A1* 2/2007 Izatt et al. .................. 356/479

FOREIGN PATENT DOCUMENTS

| EP | 1 669 021 A1 | | 6/2006 |
|---|---|---|---|
| JP | 2002-214125 A | | 7/2002 |
| JP | 2007-163241 A | * | 6/2007 |
| WO | 2004/111929 A2 | | 12/2004 |

OTHER PUBLICATIONS

Schmitt et al., "Differential absorption imaging with optical coherence tomography," J. Opt. Soc. Am. A., vol. 15, No. 9, Sep. 1998, pp. 2288-2296, XP002474885.

Gelikonov et al., "Two-Wavelength Optical Coherence Tomography," Radiophysics and Quantum Electronics, vol. 47, Nos. 10-11, Oct. 1, 2004, pp. 848-859, XP019290800.

Chinn et al., "Optical coherence tomography using a frequency-tunable optical source," Optics Letters, vol. 22, No. 5, Mar. 1, 1997, pp. 340-342, XP000684683.

M. Takeda, Optical Frequency Scanning Interference Microscopes, Optics Engineering Contact, 2003, pp. 426-432, vol. 41, No. 7.

* cited by examiner

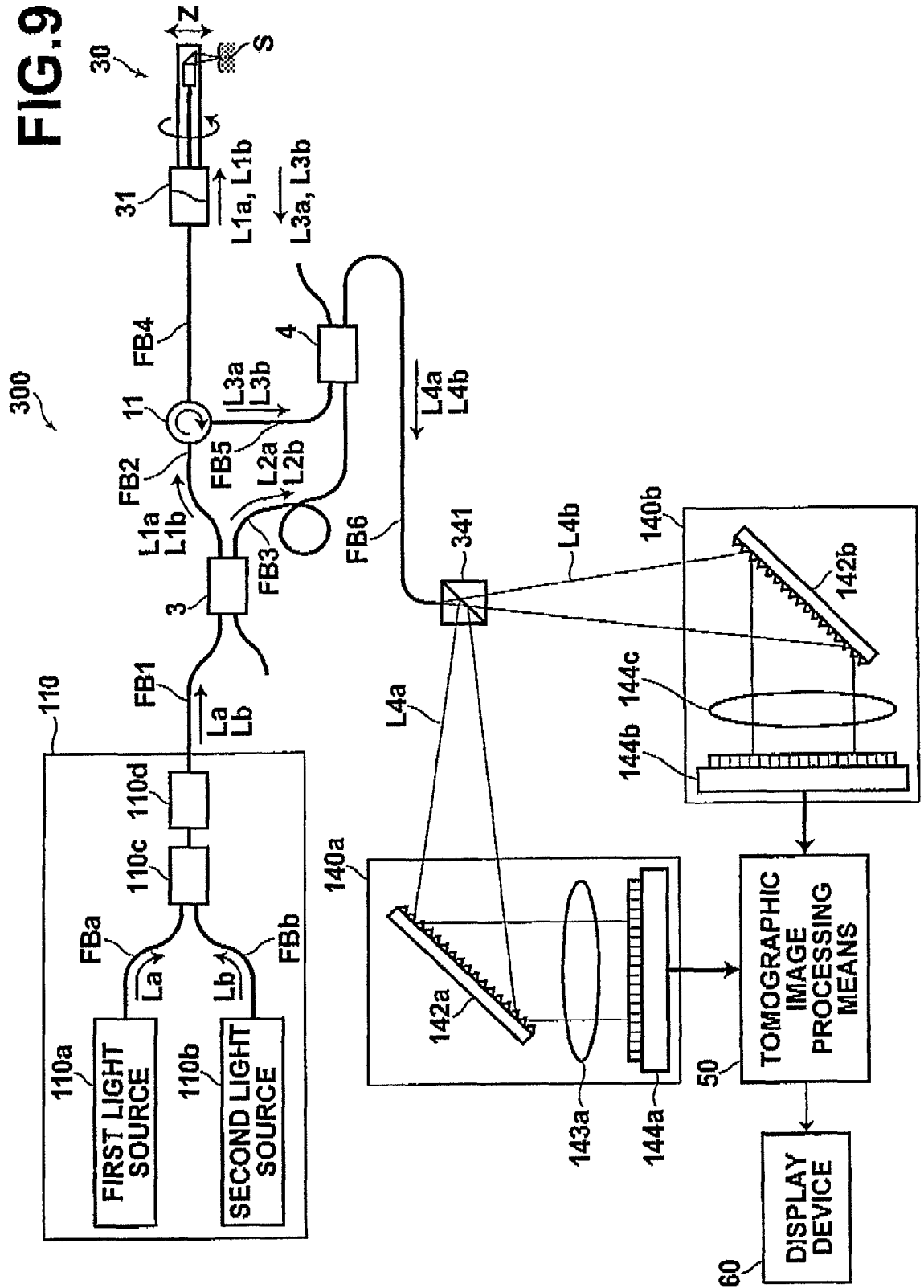

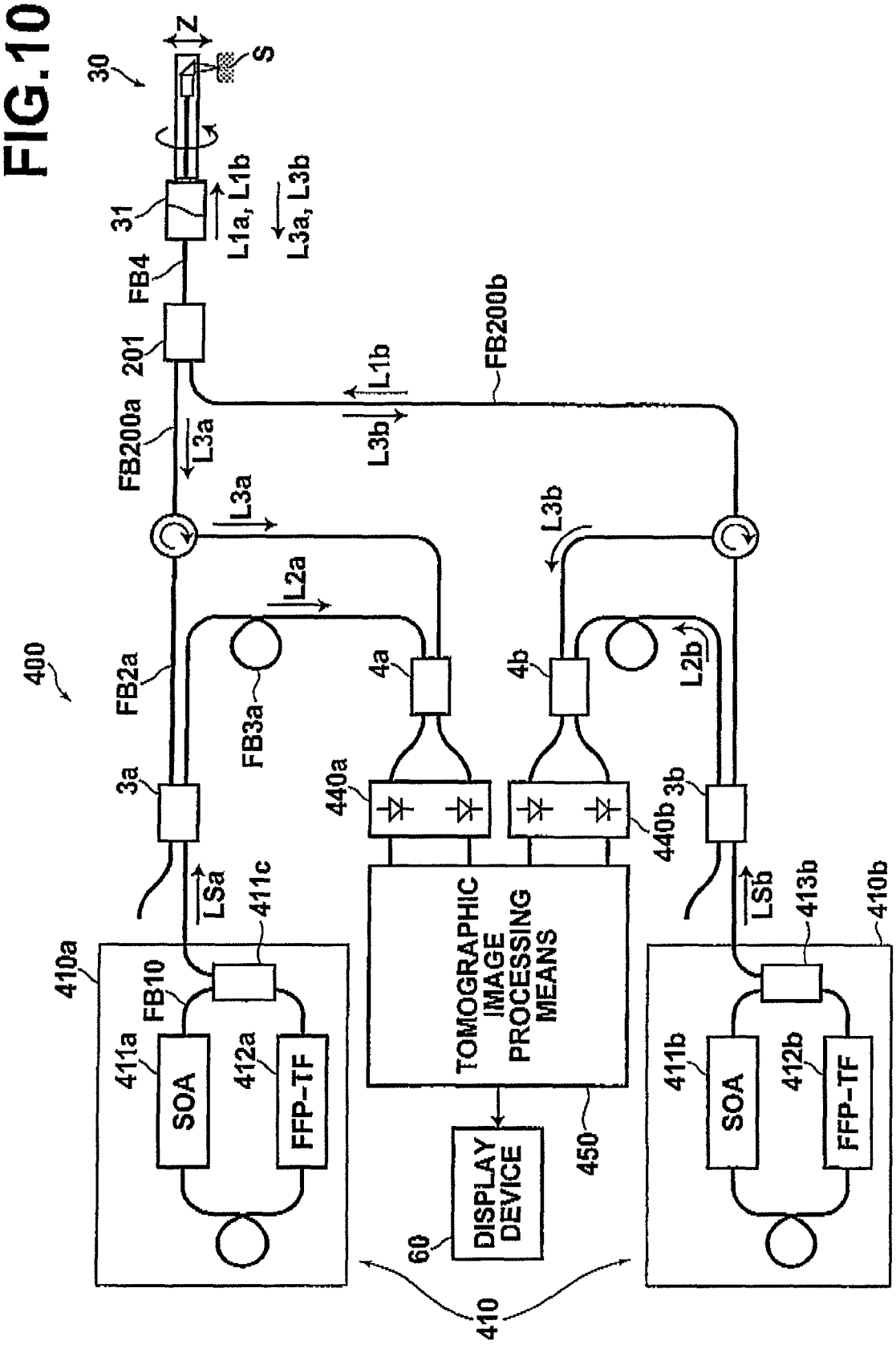

OPTICAL COHERENCE TOMOGRAPHIC IMAGING APPARATUS

BACKGROUND OF THE INVENTION

1. Field of the Invention

The present invention relates to an optical tomograph that obtains optical tomographic images by OCT (Optical Coherence Tomography) measurement.

2. Description of the Related Art

Conventionally, optical tomographs that utilize OCT measurement are used to obtain optical tomographic images of living tissue. The optical tomographs are applied to obtain tomographic images of the fundus, the anterior ocular segment, and skin. Other applications of the optical tomographs include observation of arteries employing fiber probes, and observation of digestive organs by inserting fiber probes through forceps channels of endoscopes. In these optical tomographs, a low coherence light beam emitted from a light source is divided in to a measuring light beam and a reference light beam. Thereafter, a reflected light beam, which is the measuring light beam reflected or backscattered by a measurement target when the measuring light beam is irradiated onto the measurement target, is combined with the reference light beam. Tomographic images are obtained, based on the intensity of a coherent light beam obtained by combining the reflected light beam and the reference light beam.

OCT measurement can be roughly divided into two types, TD-OCT (Time Domain Optical Coherence Tomography) and FD-OCT (Fourier Domain Optical Coherence Tomography). In TD-OCT measurement, the intensity of the interference light beam is measured while changing the optical path length of the reference light beam. Thereby, intensity distributions of the reflected light beam corresponding to measuring positions in the depth direction of the measurement target (hereinafter, referred to as "depth positions") are obtained.

On the other hand, in FD-OCT measurement, the optical path lengths of the reference light beam and the signal light beam are not changed. The intensity of the interference light beam is measured for each spectral component thereof, and frequency analysis, such as Fourier transform, is administered on the obtained spectral interference intensity signals. Thereby, intensity distributions of the reflected light beam corresponding to the depth positions of the measurement target are obtained. FD-OCT measurement has been gathering attention recently as a method that enables high speed measurement, due to the mechanical scanning associated with TD-OCT measurement being obviated.

Optical tomographs that perform SD-OCT (Spectral Domain Optical Coherence Tomography) measurement and optical tomographs that perform SS-OCT (Swept Source Optical Coherence Tomography) measurement are two types of optical tomographs that employ FD-OCT measurement. In an SD-OCT optical tomograph, a wide band low coherence light beam is emitted from an SLD (Super Luminescent Diode), an ASE (Amplified Spontaneous Emission) light source, or a white light source. The wide band low coherence light beam is divided into a measuring light beam and a reference light beam by a Michelson interferometer or the like. Thereafter, the measuring light beam is irradiated onto a measurement target, and a reflected light beam reflected by the measurement target is caused to interfere with the reference light beam. The interference light beam formed thereby is spectrally decomposed into each frequency component by a spectrometer, and the intensity of each frequency component of the interference light beam is measured by a detector array, in which elements such as photodiodes are provided in an array. A computer administers Fourier transform on the obtained spectral interference intensity signals, to obtain a tomographic image (refer to U.S. Patent Application Publication No. 20050018201). U.S. Patent Application Publication No. 20050018201 further discloses a method in which the interference light beam is spectrally decomposed into spectral bands, and the spectrally decomposed interference light beams are respectively detected by separate photodetectors, in order to improve detection accuracy.

Further, U.S. Patent Application Publication No. 20050018201 proposes an optical tomograph that utilizes SS-OCT measurement, as an apparatus that obtains optical tomographic images at high speed without changing the optical path length of a reference light beam. This SS-OCT optical tomograph utilizes a light source that periodically sweeps the frequency of a laser beam. Reflected light beams of each wavelength are caused to interfere with reference light beams of each wavelength. Temporal waveforms of signals corresponding to the temporal variations in the frequency of the laser beam are measured, and a computer administers Fourier transform on the obtained spectral interference intensity signals, to obtain a tomographic image.

It is desirable to employ a measuring light beam having a wide spectral width, in order to improve spatial resolution in the aforementioned TD-OCT measurement, SS-OCT measurement, and SD-OCT measurement (refer to Japanese Unexamined Patent Publication No. 2002-214125). Japanese Unexamined Patent Publication No. 2002-214125 discloses a method that widens the spectral width of the measuring light beam, in which a plurality of light sources that each emit light beams having a different spectral band are used, and an optical integrator integrates the light beams emitted from the plurality of light sources, to obtain a single light beam.

However, there is demand for a system that enables obtainment of tomographic images having favorable image quality that employs a light source having a simple structure, as opposed to the combination of light sources as disclosed in Japanese Unexamined Patent Publication No. 2002-214125, which requires stringent control.

SUMMARY OF THE INVENTION

The present invention has been developed in view of the foregoing point. It is an object of the present invention to provide an optical tomograph that employs a light source having a simple structure and enables obtainment of tomographic images having favorable image quality.

An optical tomograph of the present invention comprises:

a light source unit for emitting a plurality of light beams, each of which has a continuous spectrum within discrete wavelength bands, respectively;

light dividing means, for dividing each of the light beams emitted from the light source unit into a measuring light beam and a reference light beam;

combining means, for combining reflected light beams, which are the measuring light beams reflected by a measurement target when the measuring light beams are irradiated thereon, with the reference light beams divided by the light dividing means;

interference light detecting means, for detecting an interference light beam, which is formed by the reflected light beam and the reference light beam being combined by the combining means, for each of the light beams as an interference signal; and tomographic image processing means, for generating a tomographic image of the measurement target employing the plurality of interference signals detected by the interference light detecting means.

Here, the light source unit maybe of any construction as long as it emits a plurality of light beams. For example, the light source unit may be constituted by an ASE light source that emits a plurality of discrete light beams along a single optical path, or by a plurality of light sources that each emit a light beam of a discrete wavelength band and an optical integrator, for integrating and emitting the light beams emitted from each of the light sources. Further, the light source unit may further comprise an optical separating means, for shielding light of wavelength bands between those of the plurality of light beams, and for causing the plurality of light beams to be emitted toward the light dividing means.

Note that the widths of the wavelength bands of each light beam may or may not be uniform. The widths of the wavelength bands of each of the light beams are not limited, as long as the wavelength bands are discrete from each other.

Further, the plurality of measuring light beams may be irradiated simultaneously on the same portion of the measurement target. In this case, the optical tomograph may further comprise: a reflected light separating means, for separating the reflected light beam reflected by the measurement target for each of the light beams emitted from the light source unit. At this time, separate combining means for combining the reflected light beams and the reference light beams corresponding to each of the reflected light beams separated by the reflected light separating means; and a plurality of interference light detecting means, for respectively detecting each of the interference light beams, formed by each of the combining means, may also be provided.

Alternatively, in the case that the plurality of measuring light beams are irradiated simultaneously on the same portion of the measurement target, the optical tomograph may further comprise: an interference light separating means, for separating the interference light beam, formed by the combining means combining the reflected light beams and the reference light beams for each of the light beams emitted from the light source unit. At this time, a plurality of interference light detecting means, for respectively detecting each of the interference light beams, separated by the interference light separating means, may also be provided.

Note that the optical tomograph may obtain tomographic images by SD-OCT measurement, in which each of the light beams is a low coherence light beam. Alternatively, the optical tomograph may obtain tomographic images by SS-OCT measurement, in which each of the plurality of light beams emitted from the light source unit is a laser beam, of which the wavelength is swept at a predetermined period within the respective wavelength band thereof. As a further alternative, the optical tomograph may obtain tomographic images by a combination of SD-OCT measurement and SS-OCT measurement, in which sets of light beams from among the plurality of light beams are either low coherence light beams or light beams, of which the wavelengths are swept.

Note that in the present specification, the term "discrete wavelength bands" refers to the wavelength bands of two light beams having a wavelength band having a light intensity of approximately −10 db with respect to the peak wavelengths of the two light beams. That is, "discrete wavelength bands" refer to wavelength bands having a wavelength band having an intensity too low to contribute to OCT measurement therebetween. In the case that the peak intensities of the two light beams are different, the lower peak intensity is employed to calculate the difference between the peak intensity and the low intensity wavelength band.

Similarly, the term "continuous spectrum" refers to the spectrum of a light beam, in which a low intensity wavelength band having an intensity of approximately −10 db with respect to the peak intensity of the light beam, is not present within a wavelength band sufficiently greater than a frequency band sampling interval, which is measured in FD-OCT measurement. That is, the "continuous spectrum" is a spectrum in which there are no wavelength bands having an intensity too low to contribute to OCT measurement, within a wavelength band sufficiently greater than the frequency band sampling interval. Note that in light beams such as those emitted by semiconductor lasers, in which the frequency are modulated in a stepped manner, and those emitted by light sources that employ frequency combs to emit light beams having wide bands of densely arranged linear spectra, the intervals between the discrete wavelength bands are equal to or narrower than the frequency sampling intervals measured in FD-OCT measurement. Therefore, such light beams are considered to have continuous spectra.

In the present specification, the term "spectrum" refers not to an instantaneous spectrum, but the distribution of light intensities with respect to wavelengths over the entire time that the light beams are being emitted, unless otherwise noted.

The optical tomograph of the present invention comprises: a light source unit for emitting a plurality of light beams, each of which has a continuous spectrum within discrete wavelength bands, respectively; light dividing means, for dividing each of the light beams emitted from the light source unit into a measuring light beam and a reference light beam; combining means, for combining reflected light beams, which are the measuring light beams reflected by a measurement target when the measuring light beams are irradiated thereon, with the reference light beams divided by the light dividing means; interference light detecting means, for detecting an interference light beam, which is formed by the reflected light beam and the reference light beam being combined by the combining means, for each of the light beams as an interference signal; and tomographic image processing means, for generating a tomographic image of the measurement target employing the plurality of interference signals detected by the interference light detecting means. Therefore, obtainment of tomographic images having image quality as high as that in a case in which a light source that emits a wide band continuous spectrum light beam is enabled, by employing a light source unit having a simple structure that emits a plurality of light beams and employing the interference signals obtained thereby.

Note that if the light source unit is constituted by an ASE light source that emits a plurality of discrete light beams, tomographic images having high image quality can be obtained by a light source unit having a simple structure.

Alternatively, if the light source unit is constituted by a plurality of light sources that emit light beams each having a discrete wavelength band, and an optical integrator that integrates and emits the light beams emitted by each of the light sources, tomographic images having high image quality can be obtained by a light source unit having a simple structure.

Further, if the plurality of measuring light beams are irradiated simultaneously on the same portion of the measurement target, the optical tomograph may further comprise: a reflected light separating means, for separating the reflected light beam reflected by the measurement target for each of the light beams emitted from the light source unit. Separate combining means for combining the reflected light beams and the reference light beams corresponding to each of the reflected light beams separated by the reflected light separating means; and a plurality of interference light detecting means, for respectively detecting each of the interference light beams, formed by each of the combining means, may also be provided. In this case, each of the interference light detecting means can be of a specialized structure for detecting the interference light beam corresponding to the wavelength band of each light beam. Therefore, the detection accuracy of the interference light detecting means can be improved, thereby improving the resolution of the tomographic image.

Alternatively, if the plurality of measuring light beams are irradiated simultaneously on the same portion of the measurement target, the optical tomograph may further comprise: an interference light separating means, for separating the interference light beam, formed by the combining means combining the reflected light beams and the reference light beams for each of the light beams emitted from the light source unit. A plurality of interference light detecting means, for respectively detecting each of the interference light beams, separated by the interference light separating means, may also be provided. In this case, each of the interference light detecting means can be of a specialized structure for detecting the interference light beam corresponding to the wavelength band of each light beam. Therefore, the detection accuracy of the interference light detecting means can be improved, thereby improving the resolution of the tomographic image.

Further, the interference light detecting means may comprise: a spectrally decomposing element, for spectrally decomposing the interference light beams; and a photodetecting section, constituted by a plurality of photodetecting elements, for photoelectrically converting each of a plurality of wavelengths of the spectrally decomposed interference light beams, to generate the interference signals. In this case, the measurement rate for individual lines can be accelerated. At the same time, the need for a single light receiving element to detect a wide band light beam is obviated, and general purpose photodetecting elements can be employed.

The light source unit may further comprise: an optical separating means, for shielding light of wavelength bands between those of the plurality of light beams, and for causing the plurality of light beams to be emitted toward the light dividing means. In this case, each of the light beams can be positively separated, and noise caused by interference light beams formed by the light beams can be prevented.

Note that the optical tomograph is capable of obtaining tomographic images having high image quality by SD-OCT measurement, in which each of the light beams is a low coherence light beam. The optical tomograph is also capable of obtaining tomographic images having high image quality by SS-OCT measurement, in which each of the plurality of light beams emitted from the light source unit is a laser beam, of which the wavelength is swept at a predetermined period within the respective wavelength band thereof.

BRIEF DESCRIPTION OF THE DRAWINGS

FIG. 9 is a diagram that illustrates the schematic construction of an optical tomograph according to a fourth embodiment of the present invention.

FIG. 10 is a diagram that illustrates the schematic construction of an optical tomograph according to a fifth embodiment of the present invention.

BEST MODE FOR CARRYING OUT THE INVENTION

Figure 1:
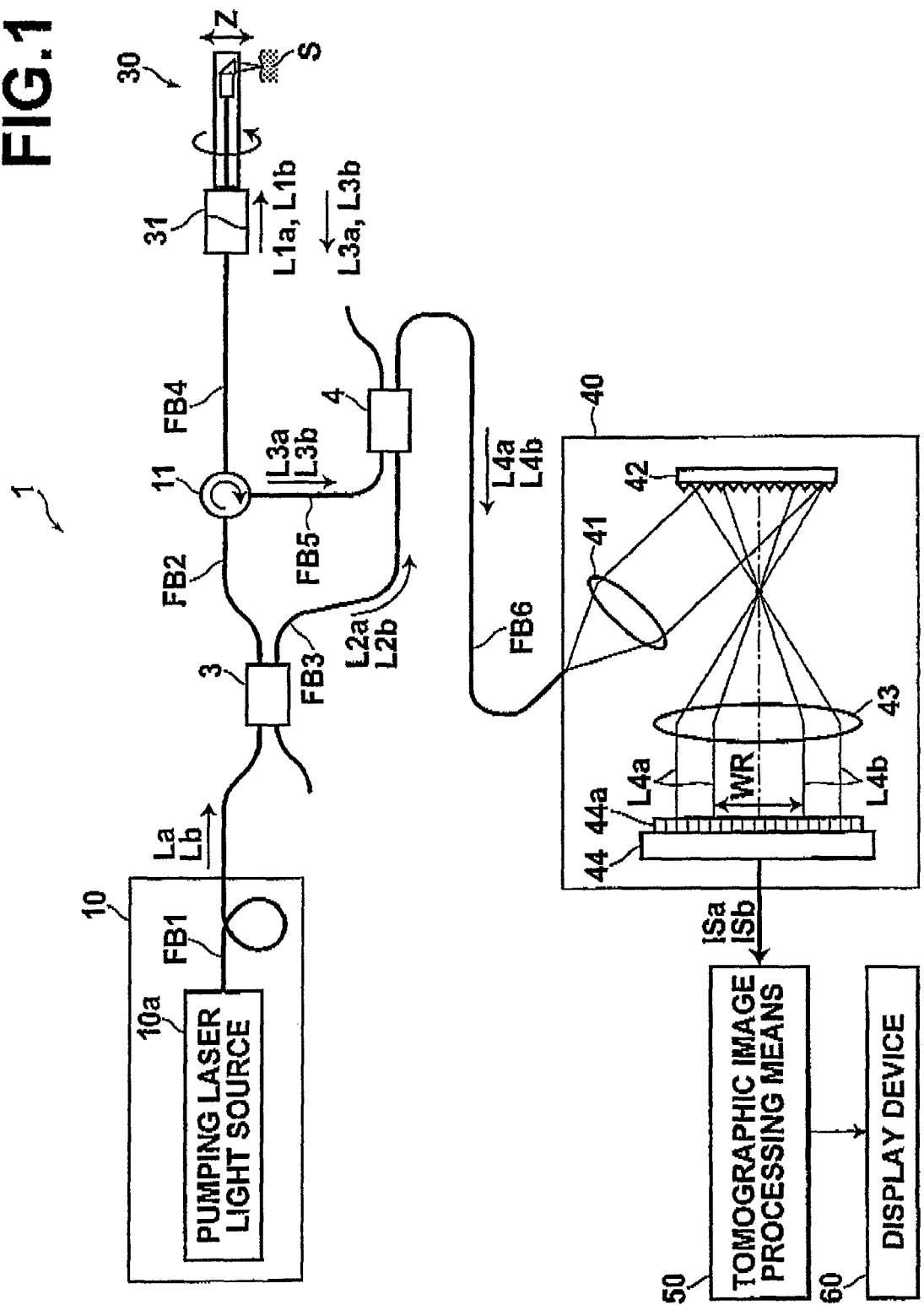
FIG. 1 is a diagram that illustrates the schematic construction of an optical tomograph according to a first embodiment of the present invention.

Hereinafter, optical tomographs according to preferred embodiments of the present invention will be described in detail with reference to the attached drawings. FIG. 1 is a diagram that illustrates the schematic construction of an optical tomograph 1 according to a first embodiment of the present invention. The optical tomograph 1 obtains tomographic images of measurement targets such as tissue within body cavities or cells by SD-OCT measurement, using a Mach-Zehnder type interferometer. The optical tomograph 1 comprises: a light source unit 10 for emitting light beams La and Lb; a light dividing means 3 for dividing the light beams La and Lb into measuring light beams L1a, L1b and reference light beams L2a, L2b; a combining means 4 for combining reflected light beams L3a, L3b, which are the measuring light beams L1a and L1b reflected by a measurement target S when irradiated thereon, with the reference light beams L2a, L2b; an interference light detecting means 40, for detecting interference light beams L4a, L4b, which are formed by the combining means 4 combining the reflected light beams L3a, L3b with the reference light beams L2a, L2b; and a tomographic image processing means 50, for detecting tomographic data (reflectance) regarding various depth positions of the measurement target S, by administering frequency analysis on the interference light beams L4a, L4b detected by the interference light detecting means 40, to obtain a tomographic image of the measurement target S.

Figure 2:
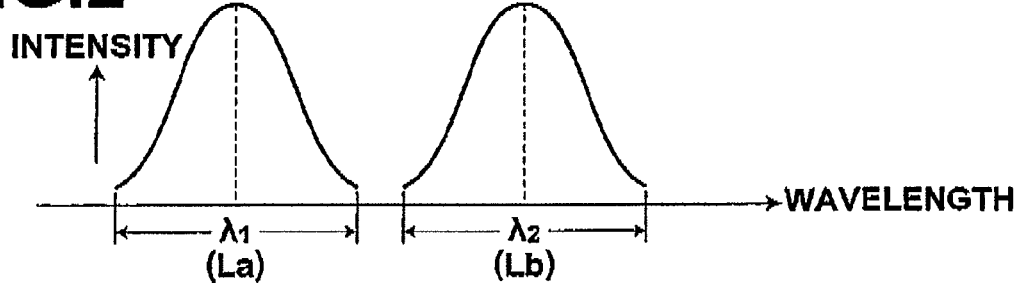
FIG. 2 is a graph that illustrates an example of a plurality of light beams emitted by a light source unit of FIG. 1.

The light source unit 10 is constituted by an ASE (Amplified Spontaneous Emission) light source, such as a rare earth ion doped fiber amplifier laser, and comprises a pumping laser light source 10a and a rare earth ion doped fiber amplifier FB1, for example. $Pr^{3+}$ that emits light within a wavelength band from 1.25 µm to 1.35 µm, $Tm^{3+}$ that emits light within a wavelength band from 1.45 µm to 1.5 µm, and $Er^{3+}$ that emits light within a wavelength band from 1.5 µm to 1.6 µm are co-doped in the fiber amplifier FB1, and there is no material that emits light within the wavelength band form 1.35 µm to 1.45 µm. Accordingly, the light source unit 10 emits the light beams La and Lb within discrete wavelength bands Δ1 and Δ2, without any light being emitted within the wavelength band of 1.35 µm to 1.45 µm, as illustrated in the graph of FIG. 2. The first light beam La, which is a low coherence light beam having a continuous spectrum within wavelength band Δ1 (1.25 µm to 1.35 µm), and the second light beam Lb, which is a low coherence light beam having a continuous spectrum within wavelength band Δ2 (1.45 µm to 1.6 µm), are emitted simultaneously along the same optical path.

The light dividing means 3 of FIG. 1 is constituted by a 2×2 optical fiber coupler, for example. The light dividing means 3 functions to divide each of the light beams La and Lb, which are emitted by the light source unit 10 and guided through the optical fiber FB1, into the measuring light beams L1a, L1b and the reference light beams L2a, L2b. The division ratio of the light dividing means 3 is measuring light beam L1: reference light beam L2=90:10, for example. The light dividing means 3 is optically connected to optical fibers FB2 and FB3. The measuring light beams L1a and L1b enter the optical fiber FB2, and the reference light beams L2a and L2b enter the optical fiber FB3.

An optical circulator 11 is connected to the optical fiber FB2, and optical fibers FB4 and FB5 are connected to the optical circulator 21. The optical fiber FB4 is connected to a probe 30 that guides the measuring light beams L1a and 11b to the measurement target S. The measuring light beams L1a and L1b are enter the probe 30 via an optical rotary connector 31, guided to the measurement target S, and simultaneously emitted onto the same portion of the measurement target S. The reflected light beams L3a and L3b, which are reflected by the measurement target S, are also guided through the probe 30. A fiber portion of the probe 30 beyond the rotary optical connector 31 is configured to be rotated by a motor (not shown), and thereby, the light beams are scanned in a circumferential direction. This scanning enables obtainment of two dimensional tomographic images. Further, a motor (not shown) is configured to scan the distal end of the probe 30 in a direction perpendicular to the plane formed by the scanning circle of the optical path of the measuring light beams L1a and L1b. Thereby, obtainment of three dimensional tomographic images is also enabled. In addition, the probe 30 is removably mounted to the optical fiber FB5 via an optical connector (not shown). Of course, the shape of the distal end of the probe 30 and the scanning method are not limited to those described above. Alternatively, two dimensional scanning may be realized by providing a high speed scanning mirror at the distal end of the probe 30, for example.

The reflected light beams L3a and L3b reflected by the measurement target S enter the optical circulator 11 via the optical fiber FB4, and are emitted toward the optical fiber FB5 form the optical circulator 11.

The combining means 4 is constituted by a 2×2 optical fiber coupler. The combining means 4 combines the reflected light beam L3a guided by the optical fiber FB5 and the reference light beam L2a guided by the optical fiber FB5. Similarly, the combining means 4 combines the reflected light beam L3b guided by the optical fiber FB5 and the reference light beam L2b guided by the optical fiber FB5. The combining means 4 emits an interference light beam L4a, formed by the reflected light beam L3a and the reference light beam L2a, and an interference light beam L4b, formed by the reflected light beam L3b and the reference light beam L2b, toward an optical fiber FB6. Note that the length of the optical fiber FB3 is set such that the optical path lengths of the measuring light beams L1a and L1b from the light dividing means 3 to the measurement initiating position of the measurement target S and back to the combining means 4 are equal to the optical path lengths of the reference light beams L2a and L2b.

The interference light detecting means 40 separates the interference light beams L4a and L4b guided thereto via the optical fiber FB6, photoelectrically converts each interference light beam, and detects interference signals ISa and ISb, corresponding to the wavelength bands Δ1 and Δ2 of the light beams La and Lb. Specifically, the interference light detecting means 40 comprises: a spectrally decomposing element 42, for spectrally decomposing the interference light beams L4a and L4b, having wavelength bands Δ1 and Δ2, respectively; and a photodetecting section 44, for detecting the interference light beams L4a and L4b, which have been spectrally decomposed by the spectrally decomposing element 42. The spectrally decomposing element 42 is constituted by a diffracting optical element, for example. The interference light beams L4a and L4b enter the spectrally decomposing element 42 from the optical fiber FB6 via a collimating lens 41, are spectrally decomposed by the spectrally decomposing element 42, and are emitted toward the photodetecting section 44 via an optical lens 43.

The photodetecting section 44 is constituted by an InGaAs photodiode array, an Si photodiode array, a CCD (Charge Coupled Device) image sensor or the like, in which a plurality of photodetecting elements 44a are arranged one dimensionally or two dimensionally. Each of the photodetecting elements 44a is configured to detect each wavelength band component of the spectrally decomposed coherent light beams L4a and L4b that enter the photodetecting section 44 via the optical lens 43, respectively. The photodetecting section 44 is configured to detect first interference signals ISa from the interference light beam L4a, and to detect second interference signals ISb from the interference light beam L4b. At this time, the interference light detecting means 40 observes interference signals ISa and ISb corresponding to each spectral component of light emitted by the light source unit 10.

The light source unit 10 emits the light beams La and Lb, which are of discrete wavelength bands. Therefore, the interference light beams L4a and L4b, which are spectrally decomposed by the spectrally decomposing element 42, enter the photodetecting section 44 in a spatially separated manner. Note that in the photodetecting section 44 of FIG. 1, the photodetecting elements 44a are provided within a region WR (at which the wavelength band from 1.35 µm to 1.45 µm is to be detected) between the spatially separated wavelength bands Δ1 and Δ2. However, the photodetecting elements 44a do not need to be provided in this region. A photodiode array which is capable of detecting light within the wavelength band Δ1 of the first light beam La and the wavelength band Δ2 of the second light beam Lb is employed in the photodetecting section 44. Therefore, in the case that light beams within the wavelength band Δ1 from 1.25 µm to 1.35 µm and within the wavelength band Δ2 from 1.45 µm to 1.6 µm are to be detected as described above, an InGaAs photodiode array is employed, for example.

The tomographic image processing means 50 administers frequency analysis on the interference signals ISa and ISb, which have been photoelectrically converted by the interference light detecting means 40, to detect a plurality of pieces of intermediate tomographic data (reflectance) ra(z) and rb(z) regarding each depth position within the measurement target S. The tomographic image processing means 50 functions to obtain a tomographic image of the measurement target S, by employing the plurality of pieces of intermediate tomographic data ra(z) and rb(z). Specifically, the tomographic image processing means 50 comprises: a frequency analyzing means 51, for detecting the pieces of intermediate tomographic data ra(z) and rb(z) at each depth position within the measurement target S, by administering frequency analysis on each of the interference signals ISa and ISb; a tomographic data processing means 52, for generating tomographic data r(z), to be employed in generating the tomographic image, from the pieces of intermediate tomographic data ra(z) and rb(z) detected by the frequency analyzing means 51; and a tomographic image generating means 53, for generating the tomographic image, employing the tomographic data r(z) generated by the tomographic data processing means 52.

The frequency analyzing means 51 comprises: a first frequency analyzing means 51a for detecting intermediate tomographic data ra(z) based on the first light beam La, by administering frequency analysis on the first interference signals ISa; and a second frequency analyzing means 51b for detecting intermediate tomographic data rb(z) based on the second light beam Lb, by administering frequency analysis on the second interference signals ISb. Here, the method by which the first frequency analyzing means 51 calculates the intermediate tomographic data ra(z) based on the first interference signals ISa will be described briefly. Note that a detailed description of this method can be found in M. Takeda, "Optical Frequency Scanning Interference Microscopes", Optics Engineering Contacts, Vol. 41, No. 7, pp. 426-432, 2003.

When the measuring light beam L1a having a spectral intensity distribution S(k) is irradiated onto the measurement target S, a light intensity I(l) detected by the interference light detecting means 40 as an interferogram, in which the interference patterns of each of the spectral components overlap, is expressed by the following formula:

$$I(k) = \int_0^\infty S(k)[1+\cos(k1)]dk \quad (1)$$

Figure 4:
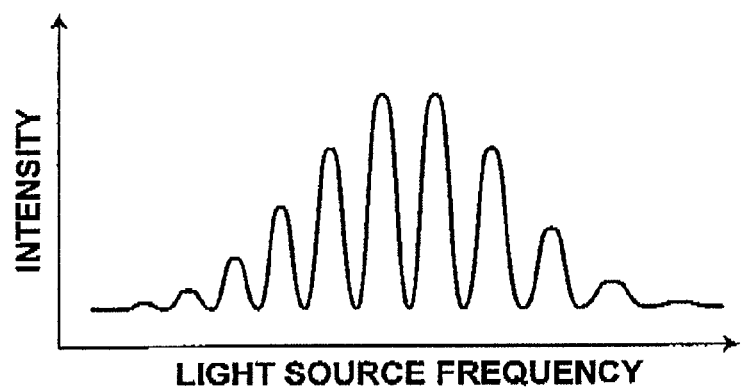
FIG. 4 is a graph that illustrates an interference light beam detected by an interference light detecting means of FIG. 1.
Figure 5:
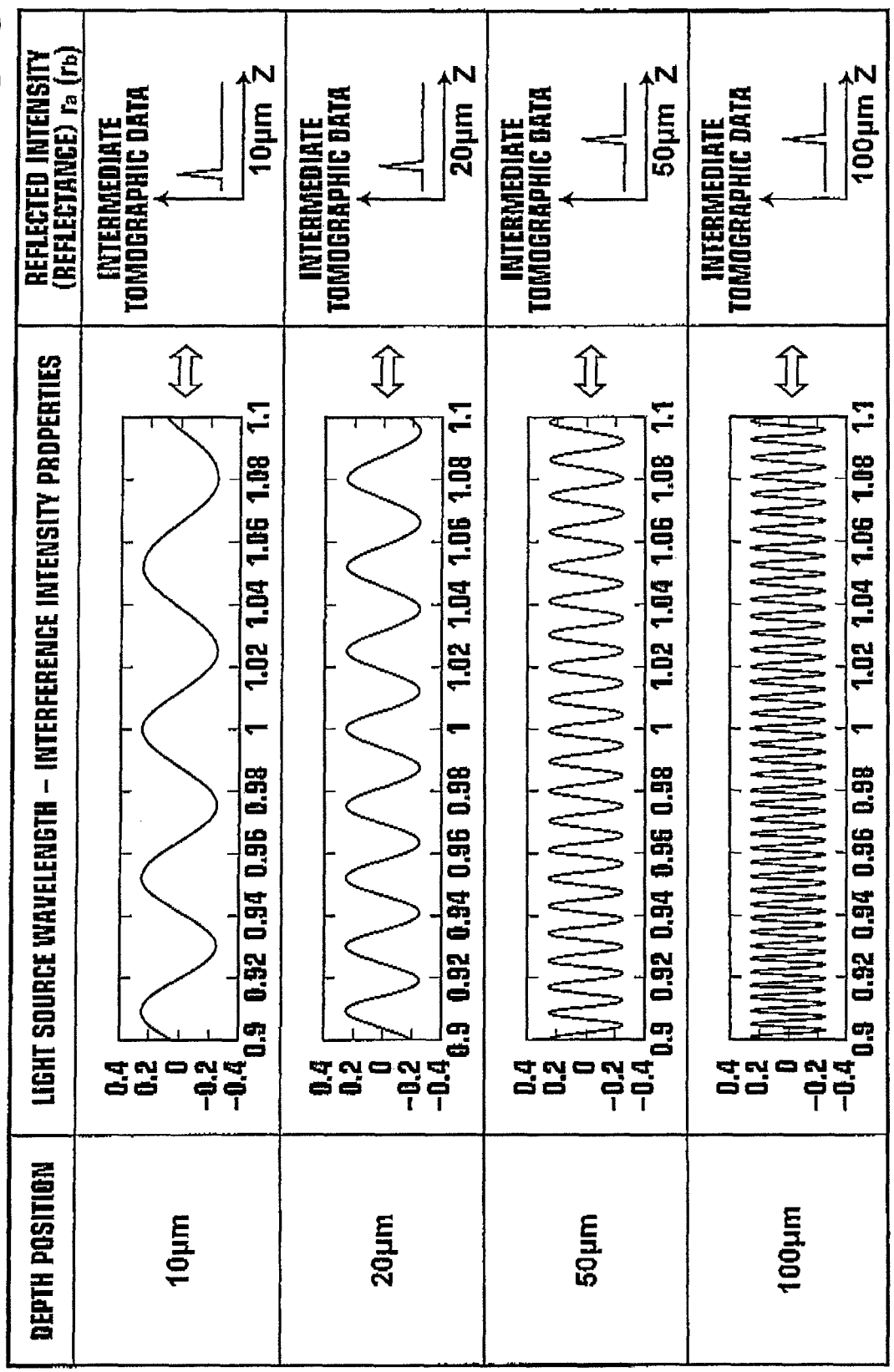
FIG. 5 is a table that illustrates tomographic data regarding each depth position within a measurement target, obtained by administering frequency analysis on the interference light beam detected by the interference light detecting means of FIG. 1.
Figure 6:
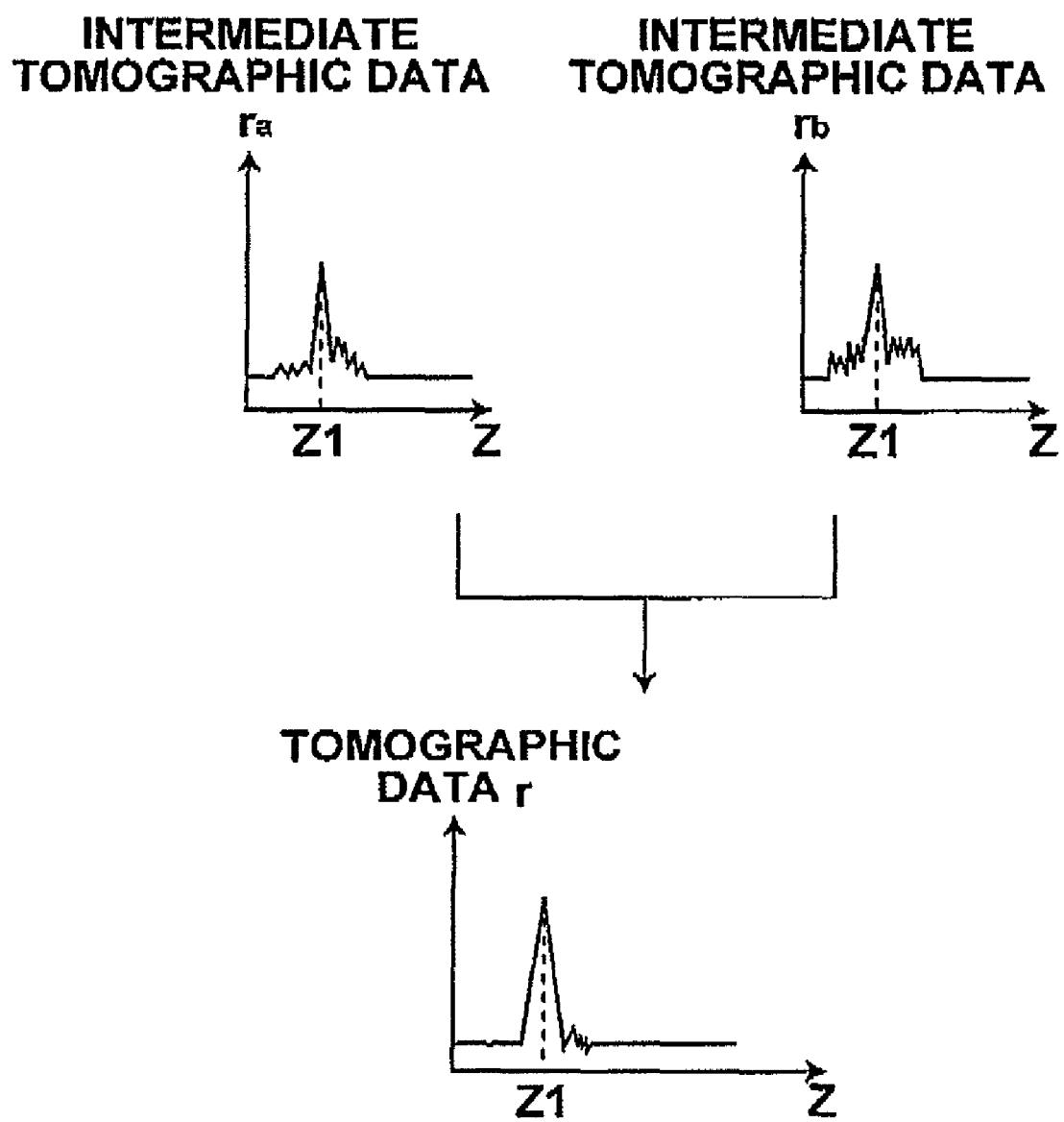
FIG. 6 is a diagram that illustrates the method by which tomographic data is generated from a plurality of pieces of intermediate tomographic data, by the tomographic image processing means of FIG. 1.

Here, k represents the angular frequency, and l represents the optical path length difference between the measuring light beam L1a and the reference light beam L2a. A example of the light intensity I(l) detected by the interference light detecting means 40 is illustrated in the graph of FIG. 4. Formula (1) above represents the amount of components having angular frequencies k within the interference pattern I(l) of the spectral intensity distribution S(k) for each spectral component. Data regarding the optical path length difference between the measuring light beam L1a and the reference light beam L2a, that is, data regarding the depth position within the measurement target S, is also obtained from the angular frequencies k of the interference pattern. For this reason, the first frequency analyzing means 51a administers Fourier transform on the interferogram detected by the interference light detecting means 40, to determine the spectra S(k) of the interference light beam L4a for each depth position, as illustrated in FIG. 5. Then, the first frequency analyzing means 51a obtains data regarding the distances from a reference position within the measurement target S, and the intermediate tomographic data ra(z). Similarly, the second frequency analyzing means 51b obtains data regarding the distances from a measurement initiating position and the intermediate tomographic data rb(z), corresponding to the interference signals ISb. That is, the frequency analyzing means 51 obtains the plurality of pieces of intermediate tomographic data ra(z) and rb(z) from the same portion of the measurement target S, onto which the measuring light beams L1a and L1b are irradiated. Note that the method by which the frequency analyzing means 51 obtains the intermediate tomographic data ra(z) and rb(z) is not limited to the aforementioned Fourier transform process.

Alternatively, other known spectral analyzing techniques, such as the Maximum Entropy Method and the Yule-Walker method may be employed.

Figure 3:
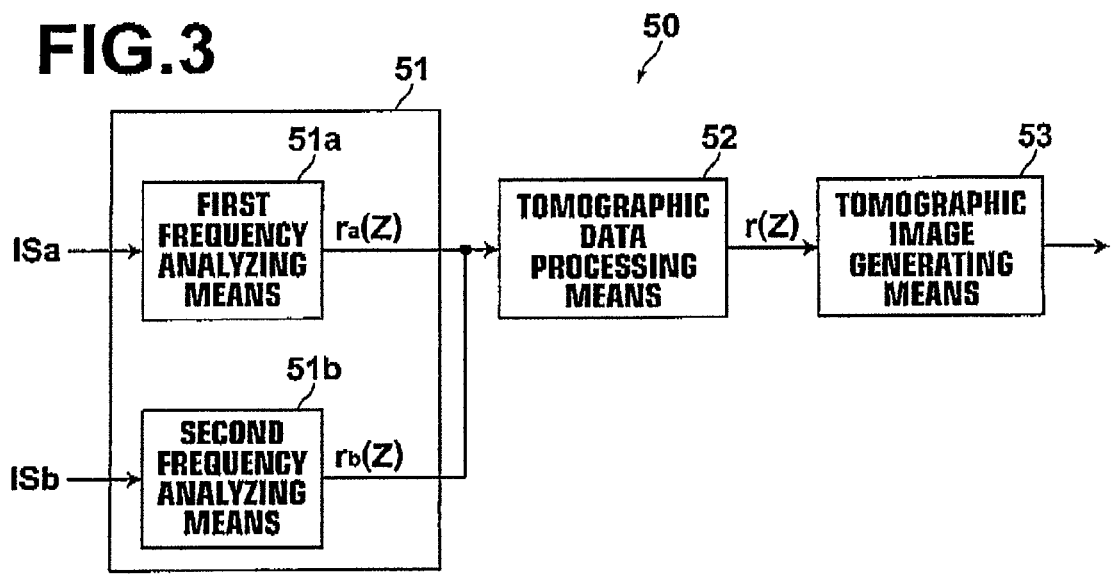
FIG. 3 is a block diagram that illustrates a example of the construction of a tomographic image processing means of FIG. 1.

The tomographic data processing means 52 illustrated in FIG. 3 detects the tomographic data r (z), which is employed to generate the tomographic image, from the plurality of pieces of intermediate tomographic data ra(z) and rb(z) detected for each depth position within the measurement target S. Specifically, the tomographic data processing means 52 calculates the tomographic data r(z) as average values of the intermediate tomographic data ra(z) and rb(z), according to the formula: $r(z) = \{ra(z)+ra(b)\}/2$.

The tomographic image generating means 53 generates the tomographic image, employing the tomographic data r(az) detected by the tomographic data processing means 52. Specifically, the measuring light beams L1a and L1b are irradiated onto the measurement target S, while being scanned in a direction perpendicular to the depth direction z thereof. Thereby, the tomographic image generating means 53 tomographic data r(z) regarding each depth position of the measurement target S at a plurality of measurement points. Thereafter, the tomographic image generating means 53 generates a two dimensional or three dimensional tomographic image, employing the obtained tomographic data r(z).

The tomographic data processing means 52 of the tomographic image processing means 50 obtains the tomographic data r(z) by calculating the average values of the plurality of pieces of intermediate tomographic data ra(z) and rb(z), as described above. Therefore, noise components and the like, which are included in each of the intermediate tomographic data ra(z) and rb(z), can be cancelled out, to improve the image quality of the generated tomographic image.

Because the measuring light beams L1a and L1b are irradiated simultaneously onto the same portion of the measurement target S, the intermediate tomographic data ra(z1) and rb(z1) obtained at a certain depth position z1 should match theoretically, even if the wavelength bands of the measuring light beams L1a and L1b are different.

In actual practice, the values of the intermediate tomographic data ra(z1) and rb(z1) obtained at a single depth position z1 may differ, due to factors such as the light absorbing properties and the light attenuating properties of the measurement target S. However, even if the values of the intermediate tomographic data ra (z) and rb (z) are different, the properties thereof (peak positions at where the tomographic data are maximal) are substantially the same.

The noise components included in the intermediate tomographic data ra(z1) and rb(z1) can be cancelled out, by calculating an average value r(z1) thereof, to emphasize the component that represents the tomographic data at the depth position z1, even if the values of the intermediate tomographic data are different. Accordingly, a tomographic image having high image quality can be obtained, even in the case that the tomographic image is obtained by employing the discrete light beams La and Lb instead of a light beam emitted by a wide band light source.

Note that the sampling pitch with respect to the Fourier transform performed by the frequency analyzing means 51 depends on the widths of the wavelength bands Δ1 and Δ2 of the light beams La and Lb. For this reason, if the widths of the wavelength bands Δ1 and Δ2 are different as described above, the sampling pitches for the interference signals ISa and ISb are also different. In this case, the widths of the wavelength bands A1 and A2 can be uniformized, by inserting 0 values to the interference signals ISa, which are obtained from the light beam La having the narrower wavelength band.

In addition, a case has been described in which the average values of the intermediate tomographic data ra(z) and rb(z) are calculated. Alternatively, the products of the intermediate tomographic data ra(z) and rb(z) may be employed as the tomographic data r(z). In this case, the highest signal components within the intermediate tomographic data ra(z) and rb(z) are reinforced by multiplication. Therefore, the signal values of noise components are relatively decreased, and tomographic images having high image quality can be obtained. Further, methods other than those described above may be employed to generate the tomographic data r(z) regarding each depth position of the measurement target S, employing the intermediate tomographic data ra(z) and rb(z). Thereafter, tomographic images constituted by pixel signals based on the tomographic data r(z) may be generated.

In the embodiment described above, a case in which the average values of the intermediate tomographic data ra(z) and rb(z) are employed to obtain the tomographic data r(z) has been described as an example. Alternatively, data regarding the spectra of the light beams La and Lb emitted by the light source unit 10 may be employed to combine the intermediate tomographic data ra(z) and rb(z) while taking the wavelength bands of the interference signals ISa and ISb. This enables obtainment of the tomographic data (reflectance intensities) r(z) at high resolution. That is, the intermediate tomographic data ra(z) and rb(z), which are obtained by administering Fourier transform on the interference signals ISa and ISb, have the following relationships with the true reflectance intensities r(z) and ha(z) and hb(z), which are the spectral shapes of the light beams La and Lb on which Fourier transform has been administered;

$$ra(z) = r(z) \otimes ha(z) \quad (2)$$

$$rb(z) = r(z) \otimes hb(z) \quad (3)$$

wherein ⊗ represents a convolution operation.

If these relationships are discretely expressed as ra=[ra(0), ra(1×dz$_a$), ... ]$^T$, rb=[rb(0), rb(1×dz$_b$), ... ]$^T$, and r=[r(0), r(1×dz), ... ] the relationships can be expressed by the following formulas:

$$Ha \cdot r = ra \quad (4)$$

$$Hb \cdot r = rb \quad (5)$$

Here, Ha and Hb are matrices constituted by each vector of ha=[ha(0), ha(1×dz), ... ] and hb=[hb(0), hb(1×dz), ... ], of which the elements are shifted while being arranged. The reflectance intensities r can be obtained as optimized solutions to these relational expressions, by known techniques such as the recursion method.

The reflectance intensities r(z) can be calculated more accurately from relational expressions that take the differences in wavelength bands of the light beams La and Lb into consideration. Therefore, higher resolution tomographic images can be generated.

Next, the operation of the optical tomograph 1 will be described with reference to FIGS. 1 through 6. First, the light beams La and Lb, which have continuous spectra within their respective wavelength bands Δ1 and Δ2, are emitted from the light source unit 10, and enter the light dividing means 3. The light dividing means 3 divides the light beams La and Lb into measuring light beams L1a, L1b and reference light beams L2a, L2b. The measuring light beams L1a and L1b are emitted toward the optical fiber FB2, and the reference light beams L2a and L2b are emitted toward the optical fiber FB3.

The measuring light beams L1a and L1b propagate through the optical circulator 11, the optical fiber FB4, and the probe 30, and is irradiated onto the measurement target S. The reflected light beams L3a and L3b, which are reflected at each depth position z within the measurement target S, as well as backscattered light, reenters the probe 30. The reflected light beams L3a and L3b enter the combining means 4, via the probe 30, the optical circulator 11, and the optical fiber FB5. Meanwhile, the reference light beams L2a and L2b enter the combining means 4 via the optical fiber FB3

The combining means 4 combines the reflected light beams L3a, L3b and the reference light beams L2a, L2b. The interference light beams L4a and L4b formed by the combining means 4 are emitted toward the optical fiber FB6. At this time, the interference light beams L4a and L4b do not interfere with each other, because the light beams La and Lb are low coherence light beams having discrete wavelength bands. The interference light beams L4a and L4b which have propagated through the optical fiber FB6 are photoelectrically converted by the photodetecting section 44 of the interference light detecting means 40, and the interference signals ISa and ISb are generated. The plurality of pieces of intermediate tomographic data ra(z) and rb(z) regarding each depth position of the measurement target S are detected from the interference signals ISa and ISb. Then, the tomographic data r(z), which is employed to generate the tomographic image, are calculated from each piece of the intermediate tomographic data ra(z) and rb(z). Finally, the two dimensional optical tomographic image is generated.

In the first embodiment, the light source unit 10 that emits the light beams La and Lb having discrete wavelength bands Δ1 and Δ2 is employed to obtain the tomographic image. Therefore, the conventional need to employ a light source that emits light having a limited specific spectral shape is obviated, ad various wide band light sources can be utilized.

That is, in conventional OCT apparatuses, it is considered ideal for the light sources to be used therein to emit light having a Gaussian spectrum. Side lobes become prominent in TD-OCT measurement, when a light source that emits light having a spectral shape other than a Gaussian shape is employed, which causes a problem that the resolution of tomographic images obtained thereby deteriorates. Meanwhile, in FD-OCT measurement such as SD-OCT measurement and SS-OCT measurement, in which spectral signals are measured, the spectrum of the light emitted by the light source is measured in advance. Then, filter functions obtained from the measured spectrum are applied to the interference signals, to approximate signals obtained from light having a Gaussian distribution. However, it is necessary for the spectrum of light corresponding to a depth range, from which tomographic images are to be obtained, to be continuous. Appropriate processing cannot be administered onto discrete spectral shapes that have light intensities of 0 at the center of a light emission band, for example (spectral shape problems).

Next, in conventional OCT apparatuses, it is desirable for the wavelength bands of light sources to be wide, in order to realize high resolution measurement. It is desirable from the viewpoint of cost to use inexpensive semiconductor light sources such as SLD's (Super Luminescent Diodes) or SOA's (Semiconductor Optical Amplifiers). However, the gain bands of these light sources are limited according to the medium properties thereof, and it is difficult to realize continuous bandwidths that exceed 100 nm using these light sources by themselves. It is possible to emit wide band low coherence light, using wide band light sources that utilize ASE fiber amplifiers, by co-doping different rare earth ions. However, it is difficult to combine the rare earth ions that enable emission of light having a continuous spectrum.

Therefore, methods, such as that disclosed in aforementioned Japanese Unexamined Patent Publication No. 2002-214125 are employed to widen the spectral width of light beams, by using a plurality of light sources that each emit light beams having a different spectral band, and integrating the light beams emitted from the plurality of light sources. For example, there is a method that uses a super continuum light source that takes advantage of the nonlinear effects of optical fibers, as disclosed by M. Szkulmowsk et al., in Optics Communications, Vol. 246, Issues 4-6, pp. 569-578, 2005. However, this light source is large and expensive. A method in which the wavelength band of a light source is widened by combining a plurality of gain media having gain wavelength bands that are close to each other has been proposed in Japanese Unexamined Patent Publication No. 2001-025425. In this method, an optical coupler is employed to combine the light beams emitted from a plurality of SLD light sources. However, the output of the light beam emitted from the optical coupler is half the total output of the combined light beams, and therefore the light utilization efficiency is deteriorated (band widening problems).

That is, in the Fourier transform method of OCT measurement, it is necessary for the spectrum of light emitted from a light source to be continuous and wide. Therefore, it had heretofore been considered that a light source unit that emits discrete light beams is not suited as a light source to be employed to obtain tomographic images in conventional OCT apparatuses.

However, the optical tomograph 1 of FIG. 1 is capable of obtaining high resolution tomographic images using the light source unit 10 that emits light beams La and Lb having discrete wavelength bands, instead of a light source that emits light having a wide wavelength band. For this reason, the need to employ light source units which are to have the aforementioned specific properties is obviated. Further, the tomographic image processing means 50 generates the tomographic image from the pluralities of pieces of intermediate tomographic data. Accordingly, high resolution tomographic images without side lobes can be obtained, even though the light source unit that emits light having discrete spectra is employed.

Figure 7:
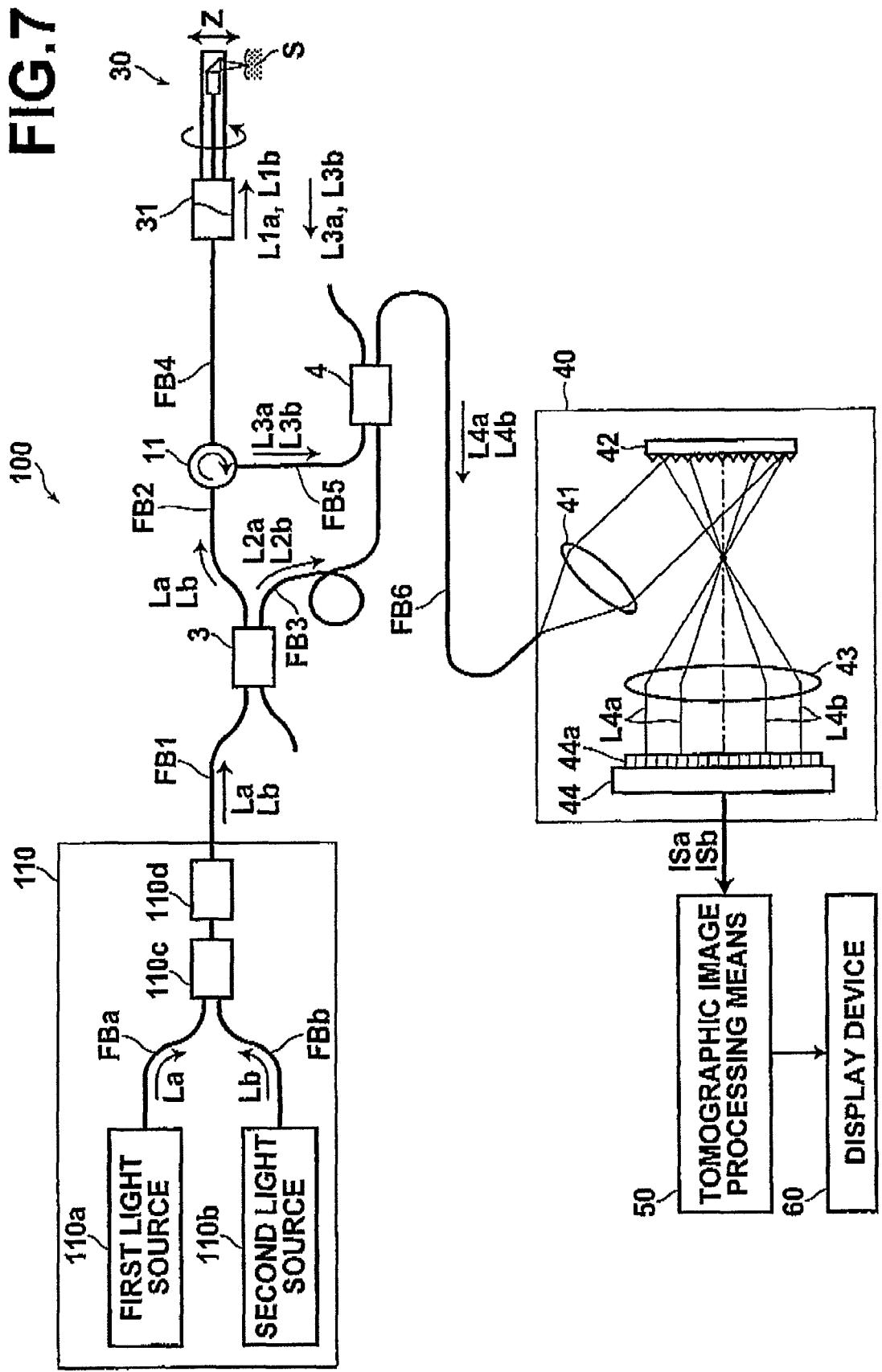
FIG. 7 is a diagram that illustrates the schematic construction of an optical tomograph according to a second embodiment of the present invention.

FIG. 7 is a diagram that illustrates the schematic construction of an optical tomograph 100 according to a second embodiment of the present invention. Note that components of the optical tomograph 100 which are the same as those of the optical tomograph 1 of FIG. 1 are denoted with the same reference numerals, and that detailed descriptions thereof will be omitted, insofar as they are not particularly necessary.

The optical tomograph 100 of FIG. 1 differs from the optical tomograph 1 of FIG. 1 in the structure of the light source unit. A light source unit 110 of the optical tomograph 100 comprises; light sources 110a and 110b, for respectively emitting light beams La and Lb which have continuous spectra within wavelength bands Δ1 and Δ2; an optical integrator 110C, for integrating the light beams La and Lb emitted by the light sources 110a and 110b; and a light separating means 110d, for separating the light beams La and Lb, which have been integrated by the optical integrator 110c, into wavelength bands Δ1 and Δ2. The light sources 110a and 110b emit light beams La and Lb, each having a discrete wavelength band, respectively (refer to FIG. 2). For example, the first light source 110a is an AlGaAs SLD that emits the light beam La having a wavelength band Δ1 of 770 nm-810 nm, and the second light source 110b is an InGaAs SLD that emits the light beam Lb having a wavelength band Δ2 of 980 nm-1020 nm.

The optical integrator 110c is constituted by a WDM (Wavelength Division Multiplexing) coupler, for example. The light beams La and Lb enter the optical integrator 110c via optical fibers Fba and FBb, are integrated by the optical integrator 110c, and are emitted toward an optical fiber FB1. Note that the optical fiber FB1 is a standard optical fiber, and not that which is doped with rare earth ions. Here, the optical integrator 110c cuts off wavelengths between the wavelength band Δ1 and Δ2. Thereby, the light beams La and Lb can be combined without suffering any light loss, and interference between the light beams La and Lb can also be prevented. In the case that the number N of light sources is three or greater, N WDM couplers may be employed to minimize deterioration of light utilization efficiency.

The light separating means 110d is constituted by a band pass filter or a band cutoff filter, for example, that transmits light beams within the wavelength bands Δ1 and Δ2, while cutting off light in other wavelength bands. Accordingly, the light beams La and Lb, which are integrated by the optical integrator 110c, enter the light separating means 110d, and are emitted toward the optical fiber FB1 as separate light beams La and Lb each having a wavelength band of Δ1 and Δ2.

Therefore, when the light beam La is emitted toward the optical fiber FBa from the first light source 110a and the light beam Lb is emitted toward the optical fiber FBb, the light beams La and Lb that respectively propagate through the optical fibers FBa and FBb are integrated by the optical integrator 110c. Thereafter, the integrated light beam enters the light separating means, and is emitted toward the optical fiber FB1 as a light beam having the wavelength band Δ1 of the light beam La and a light beam having the wavelength band Δ2 of the light beam Lb. Then, the interference signals ISa and ISb are detected in the same manner as in the optical tomograph 1 of FIG. 1, and tomographic images are obtained. Tomographic images having high image quality equivalent to that obtained by wide band light sources can be obtained by the structure of FIG. 7, in which light beams having separated spectra emitted from a plurality of light sources are combined.

Further, in the case that the configuration comprising the plurality of light sources 110a and 110b is adopted, switching from an inexpensive low resolution light source unit that employs a low number of light sources and an expensive high resolution light source unit that employs a high number of light sources according to the needs of tomographic imaging can be facilitated.

Figure 8:
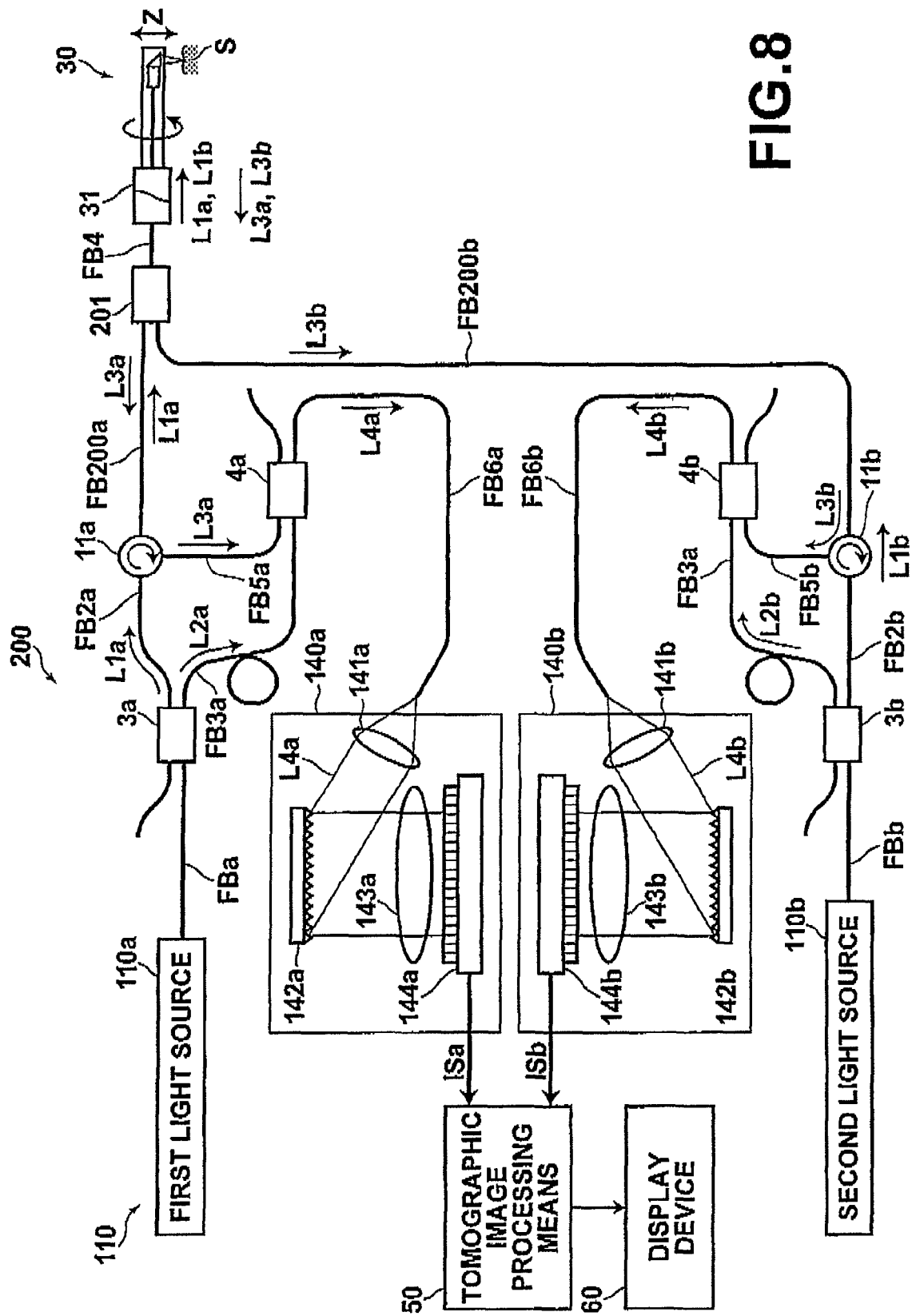
FIG. 8 is a diagram that illustrates the schematic construction of an optical tomograph according to a third embodiment of the present invention.

FIG. 8 is a diagram that illustrates the schematic construction of an optical tomograph 200 according to a third embodiment of the present invention. Note that components of the optical tomograph 200 which are the same as those of the optical tomograph 100 of FIG. 7 are denoted with the same reference numerals, and that detailed descriptions thereof will be omitted, insofar as they are not particularly necessary. The optical tomograph 200 of FIG. 8 differs from the optical tomograph 100 of FIG. 7 in that the measuring light beams L1a and L1b are simultaneously irradiated onto the same portion of the measurement target S, and that a interferometer is provided for each of the measuring light beams L1a and L1b.

Specifically, the optical tomograph 200 comprises a reflected light separating means 201 that separates the reflected light beams L3a and L3b, which are reflected from each depth position within the measurement target S, into wavelength bands Δ1 and Δ2. In the optical tomograph 200, the first light source 110a is an AlGaAs SLD that emits the light beam La having a wavelength band Δ1 of 770 nm-810 nm, and the second light source 110*b* is an InGaAsP SLD that emits the light beam Lb having a wavelength band Δ2 of 1380 nm-1420 nm, for example. Further, a plurality of combining means 3*a* and 3*b* are provided, to combine the reflected light beams L3*a* and L3*b*, which are separated by the reflected light separating means 201, and the reference light beams L2*a* and L2*b*. Still further, a plurality of interference light detecting means 140*a* and 140*b* are provided, to respectively detect the interference light beam L4*a* formed by the reflected light beam L3*a* and the reference light beam L2*a*, and the interference light beam L4*b* formed by the reflected light beam L3*b* and the reference light beam L2*b*.

Here, the light beam La which is emitted by the first light source 110*a* enters a light dividing means 3*a* via the optical fiber FBa, and is divided into the measuring light beam L1*a* and the reference light beam L2*a*. Then, the measuring light beam L1*a* propagates through a optical circulator 11*a* and an optical fiber FB200*a*, to enter an optical integrator 201 (the reflected light separating means). Note that BIG ($Bi_3Fe_5O_{12}$) is employed as the optical circulator 11*a*, for example.

Meanwhile, the light beam Lb which is emitted by the second light source 110*b* enters a light dividing means 3*b* via the optical fiber FBb, and is divided into the measuring light beam L1*b* and the reference light beam L2*b*. Then, the measuring light beam L1*b* propagates through a optical circulator 11*b* and an optical fiber FB200*b*, to enter the optical integrator 201 (the reflected light separating means). Note that YIG is employed as the optical circulator 11*b*, for example.

The optical integrator 201 (the reflected light separating means) is constituted by a WDM coupler, for example, and is configured to combine the two measuring light beams L1*a* and L1*b* then emit the combined light beam toward an optical fiber FB4. The measuring light beams L1*a* and L1*b* propagate through the optical fiber FB4 and the probe 30, and are irradiated onto the measurement target S. The reflected light beams L3*a* and L3*b* enter the optical integrator 201 via the probe 30 and the optical fiber FB4. At this time, the optical integrator 201 emits the reflected light beam L3*a* having the wavelength band Δ1 of the light beam La toward the optical fiber FB200*a*, and emits the reflected light beam L3*b* having the wavelength band Δ2 of the light beam Lb toward the optical fiber FB200*b*. Accordingly, the optical integrator 201 also functions as the reflected light separating means.

The reflected light beam L3*a* enters a combining means 4*a* via the optical fiber FB200*a*, the optical circulator 11*a*, and an optical fiber FB5*a*. The combining means 4*a* combines the reflected light beam L3*a* with the reference light beam L2*a*, and the interference light beam L4*a* formed thereby enters the interference light detecting means 140*a* via an optical fiber FB6*a*. Similarly, the reflected light beam L3*b* enters a combining means 4*b* via the optical fiber FB200*b*, the optical circulator 11*b*, and an optical fiber FB5*b*. The combining means 4*b* combines the reflected light beam L3*b* with the reference light beam L2*b*, and the interference light beam L4*b* formed thereby enters the interference light detecting means 140*b* via an optical fiber FB6*b*.

The interference light detecting means 140*a* and 140*b* have structures similar to that of the interference light detecting means 40 of FIG. 1. The interference light detecting means 140*a* and 140*b* comprise; collimating lenses 141*a*, 141*b*; spectrally decomposing elements 142*a*, 142*b* (diffraction grating elements); optical lenses 143*a*, 143*b*; and photodetecting means 144*a*, 144*b*. Note that the photodetecting means 144*a*, for detecting light having the wavelength band Δ1, is constituted by an Si photodiode array, and the photodetecting means 144*b*, for detecting light having the wavelength band Δ2, is constituted by an InGaAs photodiode array. The group number of each of the diffraction grating elements 142*a* and 142*b* is also optimized to the wavelength bands Δ1 and Δ2, respectively.

A plurality of interferometers are provided, and the interference light beams L4*a* and L4*b* of the wavelength bands Δ1 and Δ2 are detected by the dedicated interference light detecting means 140*a* and 140*b* in this manner. Therefore, it is not necessary for the optical components of the photodetecting means 144*a* and 144*b* to cover wide wavelength bands. Higher quality tomographic images can be obtained, the wavelength bands can be measured independently, and the measurement rate for individual lines can be accelerated.

FIG. 9 is a diagram that illustrates the schematic construction of an optical tomograph 300 according to a fourth embodiment of the present invention. Note that components of the optical tomograph 300 which are the same as those of the optical tomograph 100 of FIG. 7 are denoted with the same reference numerals, and that detailed descriptions thereof will be omitted, insofar as they are not particularly necessary The optical tomograph 300 of FIG. 9 differs from the optical tomograph 100 of FIG. 7 and the optical tomograph 200 of FIG. 8 in that an interference light separating means 341 is provided, to separate the interference light beams L4*a* and L4*b* into the wavelength bands Δ1 and Δ2, and that the interference light detecting means 140*a* and 140*b* detect the interference light beams L4*a* and L4*b* separated by the interference light separating means 341.

The light beams La and Lb are emitted from the light source unit 110, and the reflected light beams L3*a* and L3*b*, which are reflected at various depth positions within the measurement target S, propagate through the optical fiber FB6 (refer to FIG. 7). Here, the interference light separating means 341 is constituted by a dichroic beam splitter with a cutoff wavelength of 1000 nm, for example. Light within the wavelength band of the light beam La is reflected, and light within the wavelength band of the light beam Lb is transmitted. Accordingly, the interference light beams L4*a* and L4*b* emitted from the optical fiber FB6 are separated and emitted toward the interference light detecting means 140*a* and 140*b*, respectively.

In this case as well, in which the interference light beams L4*a* and L4*b* are separated and respectively detected by the interference light detecting means 140*a* and 140*b*, it is not necessary for the optical components of the photodetecting means 144*a* and 144*b* to cover wide wavelength bands. Higher quality tomographic images can be obtained, the wavelength bands can be measured independently, and the measurement rate for individual lines can be accelerated.

Note that in the optical tomograph 300 of FIG. 9, the light source unit 110 comprising the light sources 110*a* and 110*b* is employed. Alternatively, an ASE light source such as that illustrated in FIG. 1 may be employed.

FIG. 10 is a diagram that illustrates the schematic construction of an optical tomograph 400 according to a fifth embodiment of the present invention. Note that components of the optical tomograph 400 which are the same as those of the optical tomograph 200 of FIG. 8 are denoted with the same reference numerals, and that detailed descriptions thereof will be omitted, insofar as they are not particularly necessary. The optical tomograph 400 of FIG. 10 differs from the optical tomograph 200 of FIG. 8 in the structures of the light source unit and the interference light detecting means. That is, while the optical tomograph 200 of FIG. 8 obtains tomographic images by SD-OCT measurement, the optical tomograph 400 of FIG. 10 obtains tomographic images by SS-OCT measurement.

A light source unit 410 comprises: wavelength sweeping light sources 410a and 410b that emit laser beams L while sweeping the frequencies (wavelengths) thereof within a predetermined period. Each of the wavelength sweeping light sources 410a and 410b comprises: a semiconductor optical amplifier 411 (hereinafter, simply referred to as "SOA"); an optical fiber FB10 which is connected to the SOA 411 to form a loop; and a wavelength selecting means 412, for selecting light to be emitted from the light sources 410a and 410b, by selecting a wavelength of light from among that which propagates through the optical fiber 10. The SOA's 411a and 411b function to emit a slight amount of light into a first end of the optical fibers FB10, when a drive current is injected thereinto, and to amplify the light that enters it from a second end of the optical fibers FB10. When the drive current is supplied to the SOA's 411a and 411b, the laser beams L propagate through the loops formed by the SOA's 411a and 411b and the optical fibers FB10.

Further, an optical divider 411c is linked to the optical fiber FB10, and a portion of the light beam that propagates within the optical fiber FB10 is emitted from the optical divider 411c into an optical fiber FB11. The wavelength of the light beam, which is emitted from the optical finer FB11, is selected by the wavelength selecting means 412, The wavelength selecting means 412 is constituted by a FFP-TF (Fiber Fabry-Perot Tunable Filter), for example. The wavelength selecting means 412 selects wavelengths to be emitted from the optical divider 411c such that the wavelength of the emitted light beam is swept within the predetermined period.

Figure 11A:
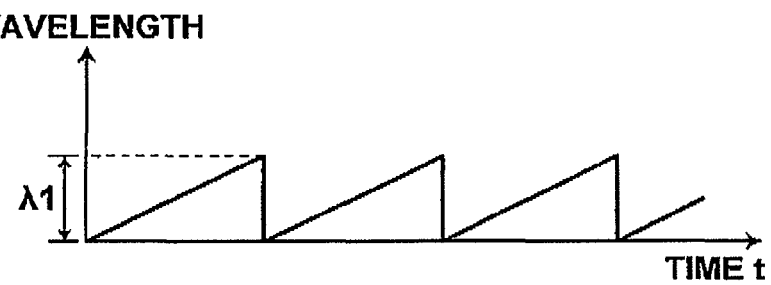
FIGS. 11A, 11B, and 11C are graphs that illustrate an example of a plurality of light beams emitted by a light source unit of FIG. 10.
Figure 11B:
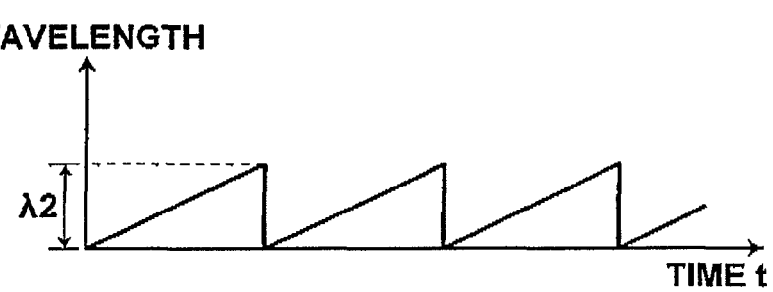
Figure 11C:
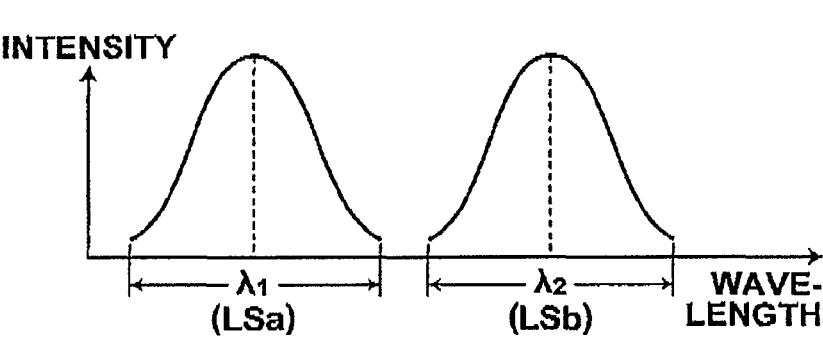

Accordingly, the wavelength sweeping light source 410a emits a first light beam LSa (laser beam), of which the wavelength is swept within the wavelength band $\Delta 1$, as illustrated in the graph of FIG. 11A. Similarly, the wavelength sweeping light source 410b emits a second light beam LSb, of which the wavelength is swept within the wavelength band $\Delta 2$, as illustrated in the graph of FIG. 11B. Further, as illustrated in FIG. 11C, the wavelength band $\Delta 1$ and the wavelength band $\Delta 2$ are discrete wavelength bands.

An interference light detecting means 440 comprises: a detecting unit 440a, for detecting the interference light beam L4a formed by the reflected light beam L3a and the reference light beam L2a; and a detecting unit 440b, for detecting the interference light beam L4b formed by the reflected light beam L3b and the reference light beam L2b. Each of the detecting units 440a and 440b are configured to perform balanced detection of the divided interference light beams L4a and L4b using two photodetecting elements each. Therefore, the influence of fluctuations in optical intensity can be suppressed, and clearer images are enabled to be obtained.

The tomographic image processing means 50 administers frequency analysis on the interference light beams L4a and L4b detected by the interference light detecting means 440, to obtain tomographic data regarding each depth position of the measurement target S. Then, the obtained tomographic data is employed to generate a tomographic image. The tomographic image processing means 50 of the optical tomograph 400 is of the same structure as that illustrated in FIG. 3.

In the case that tomographic images are obtained by SS-OCT measurement in this manner as well, tomographic images having high image quality equivalent to that obtained by wide band light sources can be obtained. In addition, the stringent control of light emission spectra over a wide band is obviated, because the plurality of gain media can be controlled independently.

That is, various conventional methods have been proposed, in which the wavelength of a light beam that enters an interferometer at a given time is limited. For example, Japanese Unexamined Patent Publication No. 2006-047264 discloses a method in which light beams emitted from a plurality of wavelength scanning light sources (each constituted by a gain medium and a wavelength selecting element) are combined. A light source controller or a switching element is employed to limit the wavelength of a light beam that enters an interferometer at a given time. As another example, U.S. Pat. No. 6,665,320 discloses a method in which light beams emitted from a plurality of gain media are combined, and a single wavelength selecting element controls the plurality of gain media, to limit the wavelength of a light beam that enters an interferometer as a given time. It is considered that combinations of gain media made from different materials would effective in widening the wavelength band. However, if different materials are used, window regions in which none of the materials have sufficient gain efficiency will be formed. If the light beams emitted from these gain media are combined, there will be wavelength bands at which output power is conspicuously low, or at which output power is zero.

On the other hand, the optical tomograph 400 of FIG. 10 tomographic images having high image quality equivalent to that obtained by wide band light sources can be obtained, without stringent control of light emission spectra over a wide band.

According to each of the embodiments described above, the optical tomographs comprise: a light source unit 10, 110, 410, for emitting a plurality of light beams La and Lb, each of which has a continuous spectrum within discrete wavelength bands $\Delta 1$ and $\Delta 2$, respectively; light dividing means 3, for dividing each of the light beams La and Lb into measuring light beams L1a, L1b and reference light beams L2a, L2b; combining means 4, for combining reflected light beams L3a, L3b, which are the measuring light beams L1a, L1b reflected by the same portion of the measurement target S, with the reference light beams L2am L2b; interference light detecting means 40, 140, 440, for detecting interference light beams L4a, L4b, which are formed by the reflected light beams L3a, L3b and the reference light beams L2a, L2b being combined by the combining means 4 as interference signals ISa, ISb; and tomographic image processing means 50, for generating a tomographic image of the measurement target S employing the plurality of interference signals ISa, ISb detected by the interference light detecting means 40, 140, 440. Therefore, obtainment of tomographic images having image quality as high as that in a case in which a light source that emits a wide band continuous spectrum light beam is enabled, by employing the light source units 10, 110, 410 having simple structures that emit a plurality of light beams La, Lb and employing the interference signals ISa, ISb obtained thereby.

Note that if the light source unit 10 is constituted by an ASE light source that emits a plurality of discrete light beams as illustrated in FIG. 1, tomographic images having high image quality can be obtained by a light source unit having a simple structure. Alternatively, if the light source unit 110 is constituted by a plurality of light sources 110a, 110b that emit light beams La, Lb each having a discrete wavelength band, and an optical integrator 110c that integrates and emits the light beams La, Lb emitted by each of the light sources, tomographic images having high image quality can be obtained by the light source unit 110 having a simple structure.

Further, the light source unit 110 may further comprise: a shielding means, for shielding light of wavelength bands between those of the plurality of light beams, and for causing the plurality of light beams to be emitted toward the light dividing means. In this case, each of the light beams can be positively separated, and noise caused by interference light beams formed by the light beams can be prevented.

In addition, the optical tomograph 200 further comprises: the reflected light separating means 201, for separating the reflected light beams L3a, L3b reflected by the measurement target S; separate combining means 4a, 4b for combining the reflected light beams L3a, L3b with the reference light beams L2a, L2b; and a plurality of interference light detecting means 140a, 140b, for respectively detecting each of the interference light beams L4a, L4b, as illustrated in FIG. 8. Thereby, each of the interference light detecting means 140a, 140b can be of a specialized structure for detecting the interference light beam L4a or L4b corresponding to the wavelength band Δ1 or Δ2. Therefore, the detection accuracy of the interference light detecting means 140a, 140b can be improved, thereby improving the resolution of the tomographic image.

The optical tomograph 300 further comprises: the interference light separating means 341, for separating the interference light beams L4a, L4b; and a plurality of interference light detecting means 140a, 140b, for respectively detecting each of the interference light beams, separated by the interference light separating means 341, as illustrated in FIG. 9. Thereby, each of the interference light detecting means 140a, 140b can be of a specialized structure for detecting the interference light beam L4a or L4b corresponding to the wavelength band Δ1 or Δ2. Therefore, the detection accuracy of the interference light detecting means 140a, 140b can be improved, thereby improving the resolution of the tomographic image.

Further, the interference light detecting means 40, 140a, 140b comprise; the spectrally decomposing element 42, 142a, 142b, for spectrally decomposing the interference light beams L4a, L4b; and a plurality of photodetecting elements, for photoelectrically converting each of a plurality of wavelengths of the spectrally decomposed interference light beams L4a, L4b. Thereby, the measurement rate for individual lines can be accelerated. At the same time, the need for a single light receiving element to detect a wide band light beam is obviated, and general purpose photodetecting elements can be employed.

Note that the optical tomographs of the present invention are capable of obtaining tomographic images having high image quality by SD-OCT measurement, in which each of the light beams is a low coherence light beam, as illustrated in FIG. 1 through FIG. 9. The optical tomograph of the present invention is also capable of obtaining tomographic images having high image quality by SS-OCT measurement, in which each of the plurality of light beams emitted from the light source unit is a laser beam, of which the wavelength is swept at a predetermined period within the respective wavelength band thereof, as illustrated in FIG. 10.

Note that the present invention is not limited to the embodiments described above. The interferometer of FIG. 1 may be a Fizeau interferometer or a Michelson interferometer instead of the Mach-Zehnder interferometer. In addition, cases in which two light beams La, Lb are employed were described in each of the above embodiments described above. However, three or more light beams may be employed.

Further, the optical tomograph of the present invention may obtain tomographic images by a combination of SD-OCT measurement and SS-OCT measurement, in which sets of light beams from among the plurality of light beams are either low coherence light beams or light beams, of which the wavelengths are swept.

An embodiment in which the wavelength band Δ1 of the first light beam La is 1.25 μm-1.35 μm and the wavelength band Δ2 of the second light beam Lb is 1.45 μm-1.6 μm was described with reference to FIG. 2. An embodiment in which the wavelength band Δ1 of the first light beam La is 770 nm-810 nm and the wavelength band Δ2 of the second light beam Lb is 1380 nm-1420 nm was described with reference to FIG. 7. However, the present invention is not limited to these wavelength bands. The wavelength bands to be utilized can be changed appropriately, according to the material of the measurement target S. For example, a light beam within a wavelength band that has little interaction with the measurement target S (for example, the 1000 m band, in which the influence of scattering by water is small) and a light beam within a wavelength band that has great interaction with the measurement target S (for example, the 800 nm band) may be combined. In this case, high resolution tomographic image data can be obtained, while spectral data regarding the measurement target, such as the absorption properties, the scattering properties, and the fluorescent properties, can also be measured.

In addition, the light source to be utilized in the optical tomograph of the present invention is not limited to those described in the above embodiments. Any low coherence light source, such as white light lamps, super continuum light sources, and ultra short pulse lasers, or any wavelength variable lasers, such as external resonator type wavelength sweeping lasers and distribution feedback type laser may be employed. The light emitting wavelength band of the light source is not limited to the wavelength bands described in the above embodiments. However, it is necessary for the wavelength band of light emitted by the light source to be that which enables OCT measurement. There is no threshold value for a specific wavelength band, but in the case that a system is assumed that has a resolution on the order of 1 mm, the frequency band of the light is on the order of 10 GHz.

The light beams La and Lb are simultaneously irradiated onto the same portion of the measurement target S in the embodiments described above. Alternatively, the emission times of the light beams La and Lb may be shifted, such that the measurement target S is irradiated by the light beams La and Lb separately.

Optical fibers are employed to guide the light beams, and optical couplers and WDM couplers are employed to combine and divide the light beams in the embodiments described above. Alternatively, bulk optical systems that combine and divide light beams spatially, such as mirrors, prisms, dichroic mirrors, and dichroic prisms, may be employed. In addition, a configuration in which light beams which have propagated through space are scanned by a galvano mirror may be employed instead of the optical fiber probe.

In the above embodiments, light which is reflected or backscattered by the measurement target is measured. In the case that the measurement target is a transparent material, such as a glass block or a transparent film, transmitted light may be measured instead of reflected light, in order to derive the planar refractive index distribution, the thickness distribution, and birefringence of the measurement target.

Further, the optical tomograph 1 of FIG. 1 is an example of a case in which the light source unit is an ASE (Amplified Spontaneous Emission) light source. Alternatively, a light source unit constituted by a semiconductor light emitting element 500 (SLD), which will be described below, may be employed.

Figure 12:
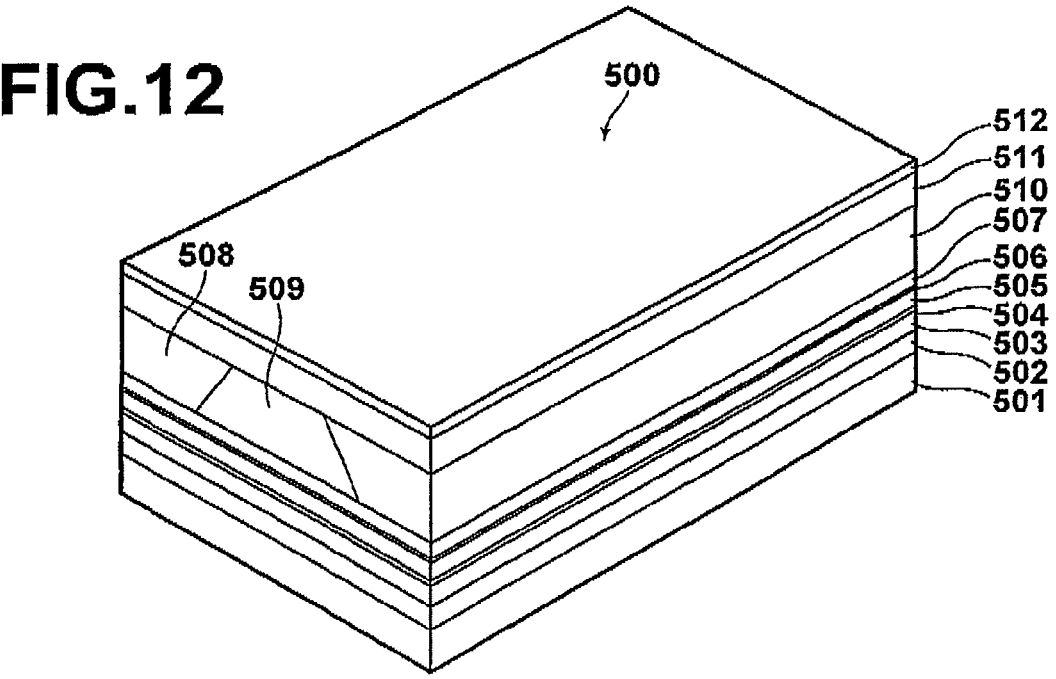
FIG. 12 is a sectional view that illustrates an example of a semiconductor light emitting element to be used in the optical tomograph of FIG. 1.

Specifically, FIG. 12 is a sectional view that illustrates an example of the semiconductor light emitting element 500. The semiconductor light emitting element 500 of FIG. 12 is an infrared light emitting SLD with an embedded ridge structure, and is produced by crystal growth using the Metal Organic chemical Vapor Deposition Method. Note that the semiconductor light emitting element 500 emits light beams L within a wavelength band within the range of 0.9 μm to 1.2 μm. Therefore, a InGaAs photodiode array, which is suited for detecting light within the above wavelength band, is employed as the photodetecting section 44.

The semiconductor light emitting element 500 is of a structure in which an n-type GaAs substrate 501, an n-type GaAs buffer layer 502 (thickness: 0.05 μm, carrier concentration: $7.0 \times 10^{17}$ cm$^{-3}$), an n-type In$_{0.49}$Ga$_{0.51}$P lower cladding layer 503 (thickness: 2.0 μm, carrier concentration: $7.0 \times 10^{17}$ cm$^{-3}$), a non doped GaAs lower optical guide layer 504 n-type In$_{0.49}$Ga$_{0.51}$P lower cladding layer 502 (thickness: 0.034 μm), a Ga$_{1-x}$In$_x$As/GaAs multiple quantum well layer 505, a non doped GaAs upper optical guide layer 506 (thickness; 0.034 μm), a first p-type In$_{0.49}$Ga$_{0.51}$P upper cladding layer 507 (thickness: 0.2 μm, carrier concentration: $7.0 \times 10^{17}$ cm$^{-3}$) a p-type GaAs etching stop layer 508 (thickness: 100 Å, carrier concentration: $7.0 \times 10^{17}$ cm$^{-3}$), a second p-type In$_{0.49}$Ga$_{0.51}$P upper cladding layer 509 (thickness; 0.5 μm, carrier concentration: $7.0 \times 10^{17}$ cm$^{-3}$), an n-type In$_{0.49}$(Al$_{0.12}$Ga$_{0.88}$)$_{0.51}$P current blocking layer 510 (thickness: 0.5 μm, carrier concentration: $10 \times 10^{18}$ cm$^{-3}$), a third p-type In$_{0.49}$(Al$_{0.12}$Ga$_{0.88}$)$_{0.51}$P upper cladding layer 511 (thickness: 1.3 μm, carrier concentration: $1.0 \times 10^{18}$ cm$^{-3}$), and a p-type GaAs contact layer 512 (thickness: 0.5 μm, carrier concentration: $1.0 \times 10^{19}$ cm$^{-3}$) are stacked in this order.

Here, the Ga$_{1-x}$In$_x$As/GaAs multiple quantum well layer 505 is constituted by three quantum well layers having uniform thicknesses. Each of the quantum well layers is formed by selecting the In composition from within a range of 0.10 to 0.25, then growing the film. At this time, the quantum well layers are set such that they emit light at wavelengths of 0.95 μm, 1.05μ, and 1.15 μm, respectively. The multiple quantum well layer 505 of the semiconductor light emitting element 500 emits light beams having two or more central wavelengths which are at least 100 nm apart from each other. The semiconductor light emitting element 500 is configured such that the spectral properties of the light beams are such that a wavelength band having an output of −6 dB the maximum output is present over 150 nm or greater, and a wavelength band having an output of −20 dB or less is present between the two central wavelengths.

The semiconductor light emitting element 500 is produced as follows. Note that TEG (Tri Ethyl Gallium), TMA (Tri Methyl Aluminum), TMI (Tri Methyl Indium), TBA (Tertial Butyl Arsine), AsH3 (arsine), PH3 (phosphine), and DMHz (Di Methyl Hydrazine) are employed as the materials of the semiconductor light emitting element 500. SiH4 (silane) and DEZ (Di Ethyl Zinc) are employed as dopants.

First, the n-type GaAs buffer layer 502, the n-type In$_{0.49}$Ga$_{0.51}$P lower cladding layer 503, and the non doped GaAs lower optical guide layer 504 are formed on the n-type GaAs substrate 501 by the MOCVD method, under conditions of growth temperature: 550° C. and growth pressure 10.3 kPa. Then, the Ga$_{1-x}$In$_x$As/GaAs multiple quantum well layer 505, constituted by the three quantum well layers, is formed by growing each quantum well layer after selecting the In composition from the range of 0.10 to 0.25.

Thereafter, the non doped GaAs upper optical guide layer 506, the first p-type In$_{0.49}$Ga$_{0.51}$P upper cladding layer 507, the p-type GaAs etching stop layer 508, the second p-type In$_{0.49}$Ga$_{0.51}$P upper cladding layer 509 and a p-type GaAs cap layer (thickness: 0.1 μm, carrier concentration; $7.0 \times 10^{17}$ cm$^{-3}$) are formed in this order in a first growth operation. Next, a dielectric film made of SiO$_2$ or the like is formed as a stripe. The GaAs cap layer and the second p-type In$_{0.49}$Ga$_{0.51}$P upper cladding layer 509 are etched, using the dielectric film as a mask. Thereby, a mesa stripe shaped ridge structure, having a width of 3 μm at the bottom end, and tilted 6 degrees with respect to a direction perpendicular to a light emitting facet in order to suppress laser emission, is formed.

Next, the n type In$_{0.49}$(Al$_{0.12}$Ga$_{0.88}$)$_{0.51}$P current blocking layer 510 is formed on the p type GaAs etching stop layer 508 excluding the portion at which the dielectric film is formed, by a second crystal growth operation by a selective growth method under conditions of a growth temperature of 600° C. Further, the third p type In$_{0.49}$(Al$_{0.12}$Ga$_{0.88}$)$_{0.51}$P upper cladding layer 511 and the p type contact layer 512 are formed on the entire surface of the stripe and the current blocking layer 510 after the dielectric film and the GaAs cap layer are removed, in a third growth operation under conditions of a growth temperature of 600° C. Then, the substrate 501 is ground until the thickness of the entire SLD bar is approximately 100 μm, and a p side electrode is formed on the contact layer 512. Thereafter, the SLD bar is cut so that the resonator length thereof becomes 0.7 mm, and anti reflective films (having a reflectance of 0.5% or less with respect to light emitted from the element) are coated on the resonator surface. The SLD is mounted onto a heat sink with the pn contact portion on the bottom, so as to increase the heat dissipating effects, thus forming the semiconductor light emitting element 500.

When the semiconductor light emitting element 500 produced in the manner described above was caused to emit light, three peaks, at 1.147 μm, 1.048 μm, and 0.958 μm were observed with an output of 30 mW. At this time, the peak at 0.147 μm had the greatest intensity. In addition, a wavelength band having an output of −20 dB or less the maximum output was present between the peaks at 1.048 μm and 0.958 μm. At this time, the total width of the wavelength bands having outputs of −6 dB or greater than the maximum output was 178 nm (greater than or equal to 150 nm). Further, the central wavelengths $\Delta_c$ and the full width at half maximum value FWHM satisfied the relationships $\Delta_c^2/\text{FHWM} \leq 8$ or equivalent, $\Delta_c+(\text{FWHM}/2) \leq 1.2$ μm, and $\Delta_c-(\text{FWHM}/2) \geq 0.9$ μm. Thereby, high resolution greater than or equal to 2.5 μm can be realized.

Note that a case has been described in which the multiple quantum well layer 505 is constituted by the three quantum well layers, of which the In compositions are selected from within the range of 0.10 to 0.25. Alternatively, the thickness of the Ga$_{1-x-y}$In$_x$N$_y$As/GaAs multiple quantum well layer 505 may be kept constant, the N composition may be set at 0.05, and the In composition may be selected from within a range of 0.15 to 0.25 when growing each of the quantum well layers. In this case, the wavelengths of light emitted by the quantum well layers will be 0.95 μm, 1.05 μm, and 1.15 μm, respectively. At this time, the peak having the greatest intensity will be the peak at 1.15 μm. In addition, the total width of the wavelength bands having outputs of −6 dB or greater than the maximum output will be 178 nm.

In the semiconductor light emitting element 500 described above, the intervals between peaks were set to 100 nm. However, the present invention is not limited to this configuration, and the intervals between peaks may be set to 120 nm, 150 nm, 170 nm, 190 nm, or 210 nm.

The MOCVD method was employed as the crystal growth method during production of the semiconductor light emitting element 500. However, the present invention is not limited to this method, and other growth methods, such as molecular beam epitaxy, may be employed. Further, the materials, compositions, and layer thicknesses of the optical guide layers, the current blocking layer, and the cladding layers are merely an example of conditions under which the semiconductor light emitting element emits single mode light beams, and the present invention is not limited to the aforementioned materials, compositions, and layer thicknesses. In addition, an SLD element having an embedded ridge stripe structure was described as the embodiment of the semiconductor light emitting element. However, the present invention is not limited to this configuration, and the semiconductor light emitting element may be of an interior stripe structure.

A case has been described in which the semiconductor light emitting element 500 of FIG. 12 is employed in the optical tomograph 1 of FIG. 1, which obtains tomographic images by SD-OCT measurement. Alternatively, the semiconductor light emitting element 500 may be employed in the optical tomograph 400 of FIGS. 10 and 11, which obtains tomographic images by SS-OCT measurement. In this case, the light source unit 410 is of a structure in which the semiconductor light emitting element 500 is employed as the SOA 411. The light beam L enters a known wavelength selecting means, such as an FFP-TF, a swingable grating, or an optical filter of which the light transmissive properties are variable. Then, specific wavelengths of the light beam are selected and emitted, thereby sweeping the wavelength of the light beam L.

In this case as well, the semiconductor light emitting element 500 is designed to emit a light beam having peaks at 0.995 μm, 1.05 μm, and 1.15 μm when driven by current, and to have a total width of the wavelength bands having outputs of −6 dB or greater than the maximum output of 178 nm. Further, the sweeping central wavelength $\Delta_{sc}^2$ and the total swept wavelength width $\Delta_s$ satisfies the relationships $\Delta_{sc}^2/\Delta_s \leq 8$ or equivalent, $\Delta_{sc}+(\Delta_s/2) \leq 1.2$ μm, and $\Delta_{sc}-(\Delta_s/2) \geq 0.9$ μm. Thereby, high resolution greater than or equal to 2.5 μm can be realized.

What is claimed is:

1. An optical tomograph, comprising:
   a light source unit for emitting a plurality of light beams, each of which has a continuous spectrum within discrete wavelength bands, respectively;
   light dividing means, for dividing each of the light beams emitted from the light source unit into a measuring light beam and a reference light beam;
   combining means, for combining reflected light beams, which are the measuring light beams reflected by a measurement target when the measuring light beams are irradiated thereon, with the reference light beams divided by the light dividing means;
   interference light detecting means, for detecting an interference light beam, which is formed by the reflected light beam and the reference light beam being combined by the combining means, for each of the light beams as an interference signal; and
   tomographic image processing means, for generating a tomographic image of the measurement target employing the plurality of interference signals detected by the interference light detecting means,
   wherein:
   the plurality of measuring light beams are irradiated simultaneously on the same portion of the measurement target;
   the combining means combines the reflected light beam and the reference light beam for each of the light beams emitted from the light source unit; and
   the optical tomograph further comprises:
   an interference light separating means, for separating the interference light beam, formed by the combining means combining the reflected light beams and the reference light beams for each of the light beams emitted from the light source unit; and
   a plurality of interference light detecting means, for respectively detecting each of the interference light beams, separated by the interference light separating means.

2. An optical tomograph as defined in claim 1, wherein the light source unit comprises:
   a plurality of light sources, each of which emits a light beam having a continuous spectrum within a discrete wavelength band; and
   an optical integrator, for integrating the light beams emitted from the plurality of light sources and sending the integrated light beam toward the light dividing means.

3. An optical tomograph as defined in claim 1, wherein the interference light detecting means comprises:
   a spectrally decomposing element, for spectrally decomposing the interference light beams; and
   a photodetecting section, constituted by a plurality of photodetecting elements, for photoelectrically converting each of a plurality of wavelengths of the spectrally decomposed interference light beams, to generate the interference signals.

4. An optical tomograph as defined in claim 1, wherein the light source unit further comprises:
   an optical separating means, for shielding light of wavelength bands between those of the plurality of light beams, and for causing the plurality of light beams to be emitted toward the light dividing means.

5. An optical tomograph as defined in claim 1, wherein:
   each of the plurality of light beams emitted from the light source unit is a low coherence light beam.

6. An optical tomograph as defined in claim 1, wherein:
   each of the plurality of light beams emitted from the light source unit is a laser beam, of which the wavelength is swept within the respective wavelength band thereof.

7. An optical tomograph as defined in claim 5, wherein:
   the light source unit comprises a semiconductor light emitting element having a multiple quantum well layer constituted by a plurality of quantum well layers;
   the semiconductor light emitting element emits a light beam having two or more central wavelengths which are at least 100 nm apart from each other; and
   the spectral properties of the light beam are such that a total width of wavelength bands having an output of −6 dB the maximum output is 150 nm or greater, and a wavelength band having an output of −20 dB or less is present between the two central wavelengths.

8. An optical tomograph as defined in claim 6, wherein:
   the light source unit comprises a semiconductor light emitting element having a multiple quantum well layer constituted by a plurality of quantum well layers;
   the semiconductor light emitting element emits a light beam having two or more central wavelengths which are at least 100 nm apart from each other; and
   the spectral properties of the light beam are such that a total width of wavelength bands having an output of −6 dB the maximum output is 150 nm or greater, and a wavelength band having an output of −20 dB or less is present between the two central wavelengths.

* * * * *